(12) United States Patent
Elmaleh

(10) Patent No.: US 10,576,171 B2
(45) Date of Patent: *Mar. 3, 2020

(54) CROMOLYN DERIVATIVES AND RELATED METHODS OF IMAGING AND TREATMENT

(71) Applicant: The General Hospital Corporation, Boston, MA (US)

(72) Inventor: David R. Elmaleh, Newton, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/916,740

(22) Filed: Mar. 9, 2018

(65) Prior Publication Data

US 2018/0193492 A1 Jul. 12, 2018

Related U.S. Application Data

(63) Continuation of application No. 14/059,924, filed on Oct. 22, 2013, now Pat. No. 9,925,282, which is a continuation-in-part of application No. 13/146,842, filed as application No. PCT/US2010/022495 on Jan. 29, 2010, now Pat. No. 8,617,517.

(60) Provisional application No. 61/148,245, filed on Jan. 29, 2009.

(51) Int. Cl.
| | | |
|---|---|---|
| A61K 38/00 | (2006.01) | |
| A61P 25/28 | (2006.01) | |
| A61K 51/04 | (2006.01) | |
| C07D 311/24 | (2006.01) | |

(52) U.S. Cl.
CPC ........ *A61K 51/0421* (2013.01); *C07D 311/24* (2013.01)

(58) Field of Classification Search
None
See application file for complete search history.

(56) References Cited

U.S. PATENT DOCUMENTS

| | | | |
|---|---|---|---|
| 3,419,578 A | 12/1968 | Fitzmaurice et al. | |
| 3,634,582 A | 1/1972 | Hartley et al. | |
| 3,686,412 A | 8/1972 | Fitzmaurice et al. | |
| 3,957,965 A | 5/1976 | Hartley et al. | |
| 4,120,285 A | 10/1978 | Nugent | |
| 4,405,735 A | 9/1983 | Wiezer et al. | |
| 4,429,545 A | 2/1984 | Steinberg | |
| 4,481,206 A | 11/1984 | Spiegel et al. | |
| 4,996,296 A | 2/1991 | Pecht et al. | |
| 5,567,720 A | 10/1996 | Averback | |
| 5,594,142 A | 1/1997 | Gaa et al. | |
| 5,655,523 A | 8/1997 | Hodson et al. | |
| 5,830,920 A | 11/1998 | Chucholowski et al. | |
| 5,904,937 A | 5/1999 | Augello et al. | |
| 6,168,776 B1 | 1/2001 | Klunk et al. | |
| 6,197,963 B1 | 3/2001 | Hirschmann et al. | |
| 6,309,623 B1 | 10/2001 | Weers et al. | |
| 6,696,039 B2 | 2/2004 | Kung et al. | |
| 6,911,466 B2 | 6/2005 | Koo et al. | |
| 6,946,116 B2 | 9/2005 | Kung et al. | |
| 6,972,127 B2 | 12/2005 | Schenk | |
| 7,160,559 B1 | 1/2007 | McGee et al. | |
| 7,858,803 B2 | 12/2010 | Elmaleh et al. | |
| 8,381,454 B1 | 2/2013 | Robinson | |
| 8,613,920 B2 | 12/2013 | Lieberburg et al. | |
| 8,617,517 B2 | 12/2013 | Elmaleh et al. | |
| 8,765,742 B2 | 7/2014 | Hilfiker et al. | |
| 9,283,230 B2 | 3/2016 | Clunas et al. | |
| 9,855,276 B2 | 1/2018 | Elmaleh | |
| 9,861,608 B2 | 1/2018 | Elmaleh et al. | |
| 9,913,847 B2 | 3/2018 | Elmaleh | |
| 9,918,992 B2 | 3/2018 | Elmaleh | |
| 9,925,282 B2 | 3/2018 | Elmaleh et al. | |
| 9,968,618 B1 | 5/2018 | Elmaleh | |
| 10,058,530 B2 | 8/2018 | Elmaleh | |
| 10,188,757 B2 | 1/2019 | Elmaleh | |
| 10,245,331 B2 | 4/2019 | Elmaleh | |
| 10,251,961 B2 | 4/2019 | Elmaleh | |

(Continued)

FOREIGN PATENT DOCUMENTS

| | | |
|---|---|---|
| CA | 2408793 A1 | 12/2001 |
| CN | 101754746 A | 6/2010 |

(Continued)

OTHER PUBLICATIONS

Akiyama et al., "Inflammation and Alzheimer's disease," Neurobiol Aging, 2000; 21(3):383-421.*

(Continued)

*Primary Examiner* — Jared Barsky
(74) *Attorney, Agent, or Firm* — Foley Hoag LLP

(57) ABSTRACT

Novel cromolyn analogs useful as imaging agents for detecting atherosclerotic plaques and for treating atherosclerosis and Alzheimer's Disease, and methods of making the cromolyn analogs, are disclosed. The cromolyn analogs have the general formula:

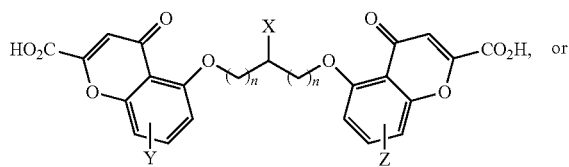

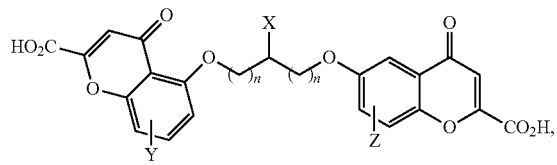

wherein: X is OH, $C_1$-$C_6$ alkoxyl; Y and Z are independently selected form a $C_1$-$C_6$ alkyl, $C_1$-$C_6$ alkoxyl, halogen, unsubstiuted or $C_1$-$C_6$ substituted amine, $^{18}F$, $^{19}F$, or H; and n is 1, 2, or 3; and wherein for structure (I), if n are both 1 and Y and Z are both H and X is OH.

10 Claims, 11 Drawing Sheets

(56) References Cited

U.S. PATENT DOCUMENTS

| | | | |
|---|---|---|---|
| 2002/0009491 A1* | 1/2002 | Rothbard | A61K 47/34 424/484 |
| 2002/0016359 A1 | 2/2002 | Hellberg et al. | |
| 2002/0091100 A1 | 7/2002 | Lezdey et al. | |
| 2002/0107173 A1 | 8/2002 | Friedhoff et al. | |
| 2004/0176469 A1 | 9/2004 | Thomas | |
| 2004/0223918 A1 | 11/2004 | Pham et al. | |
| 2004/0259952 A1 | 12/2004 | Abbas et al. | |
| 2006/0051319 A1 | 3/2006 | Yoo | |
| 2006/0159629 A1 | 7/2006 | Tarara et al. | |
| 2006/0240007 A1 | 10/2006 | Sanders | |
| 2006/0276455 A1 | 12/2006 | Lindsberg et al. | |
| 2007/0015813 A1 | 1/2007 | Carter et al. | |
| 2007/0086981 A1 | 4/2007 | Meijer et al. | |
| 2007/0093457 A1 | 4/2007 | Arber et al. | |
| 2007/0107173 A1 | 5/2007 | Yamada | |
| 2007/0178166 A1 | 8/2007 | Bernstein et al. | |
| 2007/0193577 A1 | 8/2007 | Keller | |
| 2007/0249644 A1 | 10/2007 | Pearson et al. | |
| 2007/0293538 A1 | 12/2007 | Hobden | |
| 2008/0021085 A1 | 1/2008 | Koo et al. | |
| 2009/0110679 A1 | 4/2009 | Li et al. | |
| 2009/0155256 A1 | 6/2009 | Black et al. | |
| 2010/0113613 A1 | 5/2010 | McLaurin et al. | |
| 2010/0143251 A1 | 6/2010 | Tamagnan et al. | |
| 2010/0173960 A1 | 7/2010 | Cruz et al. | |
| 2010/0234295 A1 | 9/2010 | Chen | |
| 2010/0236550 A1 | 9/2010 | Zeng et al. | |
| 2010/0266531 A1 | 10/2010 | Hsieh et al. | |
| 2010/0298389 A1 | 11/2010 | Elmaleh et al. | |
| 2011/0060138 A1 | 3/2011 | Elmaleh et al. | |
| 2011/0129530 A1 | 6/2011 | Venkatesh et al. | |
| 2011/0132434 A1 | 6/2011 | Correia et al. | |
| 2011/0262442 A1 | 10/2011 | Hamilton et al. | |
| 2012/0058049 A1 | 3/2012 | Elmaleh et al. | |
| 2012/0082727 A1 | 4/2012 | Cocconi et al. | |
| 2012/0118991 A1 | 5/2012 | Keller et al. | |
| 2012/0121656 A1 | 5/2012 | Watson et al. | |
| 2012/0134929 A1 | 5/2012 | McGrath et al. | |
| 2012/0165366 A1 | 6/2012 | Ibrahim et al. | |
| 2012/0175082 A1 | 7/2012 | Kmetovicz et al. | |
| 2014/0140927 A1 | 5/2014 | Elmaleh et al. | |
| 2014/0228304 A1 | 8/2014 | Jones et al. | |
| 2015/0224077 A1 | 8/2015 | Gerhart et al. | |
| 2015/0224078 A1 | 8/2015 | Gerhart et al. | |
| 2015/0283113 A1 | 10/2015 | Elmaleh | |
| 2016/0158150 A1 | 6/2016 | Morton et al. | |
| 2016/0310503 A1 | 10/2016 | Elmaleh | |
| 2017/0290797 A1 | 10/2017 | Elmaleh | |
| 2018/0169277 A1 | 6/2018 | Elmaleh | |
| 2018/0177789 A1 | 6/2018 | Elmaleh | |
| 2018/0177790 A1 | 6/2018 | Elmaleh | |
| 2018/0177791 A1 | 6/2018 | Elmaleh | |
| 2018/0193491 A1 | 7/2018 | Elmaleh | |
| 2018/0193492 A1 | 7/2018 | Elmaleh | |
| 2018/0344682 A1 | 12/2018 | Elmaleh | |
| 2019/0022006 A1 | 1/2019 | Elmaleh et al. | |

FOREIGN PATENT DOCUMENTS

| | | |
|---|---|---|
| CN | 101848733 A | 9/2010 |
| EP | 1632242 A2 | 3/2006 |
| EP | 2322163 A1 | 5/2011 |
| EP | 2377860 A1 | 10/2011 |
| GB | 1144906 A | 3/1969 |
| GB | 1257162 A | 12/1971 |
| JP | S56-043448 B1 | 10/1981 |
| JP | 2001151673 A | 6/2001 |
| JP | 2009-536918 A | 10/2009 |
| JP | 2012-515712 A | 7/2012 |
| WO | WO-90/09789 A2 | 9/1990 |
| WO | WO-98/34596 A2 | 8/1998 |
| WO | WO-99/16422 A1 | 4/1999 |
| WO | WO-02/28820 A1 | 4/2002 |
| WO | WO-03/045331 A2 | 6/2003 |
| WO | WO-2005/104712 A2 | 11/2005 |
| WO | WO-2007/094718 A1 | 8/2007 |
| WO | WO-2008/013799 A2 | 1/2008 |
| WO | WO-2008/061373 A1 | 5/2008 |
| WO | WO-2008/128981 A1 | 10/2008 |
| WO | WO-2008/131298 A2 | 10/2008 |
| WO | WO-2009/010770 A2 | 1/2009 |
| WO | WO-2009/133128 A1 | 11/2009 |
| WO | WO-2010/088455 A2 | 8/2010 |
| WO | WO-2011/136754 A1 | 11/2011 |
| WO | WO-2014/066318 A1 | 5/2014 |
| WO | WO-2015/002703 A1 | 1/2015 |
| WO | WO-2015061397 A1 | 4/2015 |
| WO | WO-2016/196401 A1 | 12/2016 |
| WO | WO-2017091644 A1 | 6/2017 |
| WO | WO-2018/045217 A1 | 3/2018 |

OTHER PUBLICATIONS

Aisen et al., "Effects of rofecoxib or naproxen vs placebo on Alzheimer disease progression: a randomized controlled trial," JAMA, 289(21):2819-2826 (2003).

Akiyama et al., "Inflammation and Alzheimer's Disease," Neurobiol Aging, 21(3): 383-421 (2000).

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

Aswania et al., "Relative bioavailability of sodium cromoglycate to the lung following inhalation, using urinary excretion," J Clin Pharmacol, 47:613-618 (1999).

Bannworth et al., "Stereoselective disposition of ibuprofen enantiomers in human cerebrospinal fluid.," Br J Clin Pharmacol, 40(3):266-269 (1995).

Basek et al., "Efficacy of an Isotonic Small Droplet Size Nebulized DSCG on Asthma Control in Children," Acta Paediatr, 99(Suppl 462): 115 (2010).

Beach et al., "Cromolyn sodium toxicity studies in primates," Toxicol Appl Pharmacol, 57(3):367-400 (1981).

Berg et al., "Pharmaceutical salts," J Pharm Sci, 66(1):1-19 (1977).

Bot et al., "Perivascular mast cells promote atherogenesis and induce plaque destabilization in apolipoprotein E-deficient mice," Circulation, 115(19):2516-2525 (2007).

Breitner et al., "Extended results of the Alzheimer's disease anti-inflammatory prevention trial," Alzheimers Dement, 7(4):402-411 (2011).

Breitner, "Alzheimer disease: The changing view," Annals Neurol, 49(3):418-419 (2001).

Broe et al., "Anti-inflammatory drugs protect against Alzheimer disease at low doses," Arch Neurol, 57:1586-1591 (2000).

Bulic et al., "Tau protein and tau aggregation inhibitors," Neuropharmacology, 59: 276-289 (2010).

Byron et al., "Selection and Validation of Cascade Impactor Test Methods," Respiratory Drug Delivery IX, 1: 169-178 (2004).

Cacabelos, R., "Donepezil in Alzheimer's disease: From conventional trials to pharmacogenetics," Neuropsychiatric Disease and Treatment 2007:3(3), pp. 303-333.

Cairns, et al., Synthesis and Structure-Activity Relationships of Disodium Cromoglycate and Some Related Compounds, Journal of Medicinal Chemistry, 1972, 15(6):583-589.

Chen et al., "Current experimental therapy for Alzheimer's Disease," Curr Neuropharmacol, 5(2): 127-134 (2007).

Cole et al., "Mechanisms of action of non-steroidal anti-inflammatory drugs for the prevention of Alzheimer's disease," CNS Neurol Disord Drug Targets, 9(2):140-148 (2010).

Cummings, "Alzheimer's Disease," N Engl J Med, 351(1):56-67 (2004).

(56) References Cited

OTHER PUBLICATIONS

Davies, "Clinical pharmacokinetics of ibuprofen. The first 30 years," Clin Pharmacokinet, 34(2):101-154 (1998).
Deiana, S. et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Poster Presentation (P2-428) (2009).
Doody et al., "Donepezil treatment of patients with MCI a 48-week randomized, placebo-controlled trial," Neurology, 72(18):1555-1581 (2009).
Etminan et al., "Effect of non-steroidal anti-inflammatory drugs on risk of Alzheimer9s disease: systematic review and meta-analysis of observational studies," Brit Med J, 327:128-131 (2003).
European Patent Office, Extended European Search Report, EP 10736439, dated Jun. 19, 2012, 9 pages.
European Search Report for European Application No. 14819448.3 dated Feb. 9, 2017.
Extended European Search Report issued by the European Patent Office in corresponding International Application No. 14855211.0, dated May 29, 2017.
Findeis et al., "Design and testing of inhibitors of fibril formation," Methods Enzymol, 309:476-488 (1999).
Findeis et al., "Modified-peptide inhibitors of amyloid β-peptide polymerization," Biochemistry, 38(21):6791-6800 (1999).
Galimberti et al., "Disease-modifying treatments for Alzheimer's disease," Ther Adv Neurol Disord, 4(4): 203-216 (2011).
Garmise, "Novel Dry Powder Preparations of Whole Inactivated Influenza Virus for Nasal Vaccination," Dissertation, University of North Carolina at Chapel Hill (2007).
Gasparini et al., "Non-steroidal anti-inflammatory drugs (NSAIDs) in Alzheimer's disease: old and new mechanisms of action," J Neurochem, 91(3):521-536 (2004).
Gasparini, L. et al., "Non-steroidal anti-inflammatory drugs (NSAIDs) in Alzheimer's disease: old and new mechanisms of action," Journal of Neurochemistry, 2004, 91, 521-536.
Gilani et al., "Influence of Formulation Variables and Inhalation Device on the Deposition Profiles of Cromolyn Sodium Dry Powder Aerosols," Daru vol. 12, No. 3, p. 123-130, 2004.
Griffin, "What causes Alzheimer's?" The Scientist, 25:36-40 (2011).
Guchardi, R. et al., "Influence of fine lactose and magnesium stearate on low dose dry powder inhaler formulations," International Journal of Pharmaceutics 348 (2008) 10-17.
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mal Cell Biol, 8(2):101-112 (2007).
Hashimoto et al., "Apolipoprotein E, especially apolipoprotein E4, increases the oligomerization of amyloid β peptide," J Neurosci, 32(43):15181-15192 (2012).
Heneka et al., "Acute treatment with the PPARγ agonist pioglitazone and ibuprofen reduces glial inflammation and Aβ1-42 levels in APPV717I transgenic mice," Brain, 128:1442-1453 (2005).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hori et al., "A Food and Drug Administration-approved asthma therapeutic agent impacts amyloid β in the brain in a transgenic model of Alzheimer disease," J Biol Chem, 290(4):1966-1978 (2015).
Huang et al., "Acute stress induces cardiac mast cell activation and histamine release, effects that are increased in Apolipoprotein E knockout mice.," Cardiovasc Res, 55(1):150-160 (2002).

Huang et al., "Stress-induced interleukin-6 release in mice is mast cell-dependent and more pronounced in Apolipoprotein E knockout mice," Cardiovasc Res, 59(1):241-249 (2003).
Imbimbo et al., "Are NSAIDs useful to treat Alzheimer's disease or mild cognitive impairment?," Front Aging Neurosci, 2(Article 19):pp. 1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.
Intal Approval Package, Center for Drug Evaluation and Research, pp. 1-5 (Dec. 12, 1997).
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report and Written Opinion dated Mar. 13, 2014 in connection with PCT/ US2013/066069.
International Search Report for International Application No. PCT/US14/39118 dated Sep. 18, 2014.
Jin et al., "Mast cells are early responders after hypoxia-ischemia in immature rat brain," Stroke, 40(9):3107-3112 (2009).
Karran et al., "The amyloid cascade hypothesis for Alzheimer's disease: an appraisal for the development of therapeutics," Nat Rev, 10(9):698-712 (2011).
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).
Knowles et al., "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Kotilinek et al., "Cyclooxygenase-2 inhibition improves amyloid-β-mediated suppression of memory and synaptic plasticity," Brain, 131(3):651-664 (2008).
Krstic et al., "Deciphering the mechanism underlying late-onset Alzheimer disease," Nat Rev Neurol, 9:25-34(2013).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lanz et al., "The γ-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice" The Journal of Pharmacology and Experimental Therapeutics, vol. 305, No. 3, 2003, pp. 864-871.
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience, Aug. 1, 2000, 20(15):5709-5714.
Loeb et al., "A randomized, controlled trial of doxycycline and rifampin for patients with Alzheimer's disease," J AM Geriatr Soc, 52(3): 381-7 (2004).
Mackenzie et al., "Nonsteroidal anti-inflammatory drug use and Alzheimer-type pathology in aging," Neurology, 50(4):986-990 (1998).
Mandel, "CERE-110, an adeno-associated virus-based gene delivery vector expressing human nerve growth factor for the treatment of Alzheimer's disease," Curr Opin Mol Ther, 12(2): 240-247 (2010).
Mash et al., "Loss of M2 muscarine receptors in the cerebral cortex in Alzheimer's disease and experimental cholinergic denervation," Science, 228(4703):1115-1117 (1985).
McLaurin et al., "Cyclohexanehexol inhibitors of Abeta aggregation prevent and reverse Alzheimer phenotype in a mouse model," Nat Med, 12(7):801-808 (2006).

(56) References Cited

OTHER PUBLICATIONS

Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mor et al., "Mast cells and atherosclerosis," Israel Med Assoc J, 3:216-221 (2001).
Morihara et al., "Ibuprofen Suppresses Interleukin-I13 Induction of Pro-Amyloidogenic alpha1-Antichymotrypsin to Ameliorate beta-Amyloid A-beta Pathology in Alzheimer's Models," Neuropsychopharmacology (2005) 30, 1111-1120.
Moss et al., "The absorption and clearance of disodium cromoglycate from the lung in rat, rabbit, and monkey," Toxicol Appl Pharmacol, 17(3):699-707 (1970).
Murphy, "Cromolyn sodium: basic mechanisms and clinical usage," Pediatr Asthma Aller, 2(4):237-254 (1988).
Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma—a critical review," Sleep Breath, 16:1027-1032 (2012).
Newman et al., "Therapeutic Aerosols 1—Physical and Practical Considerations," Thorax, 38(12): 881-886 (1983).
Ono et al., "Push-pull benzothiazole derivatives as probes for detecting β-amyloid plaques in Alzheimer's brains," Bioorg Med Chem, 17(18):7002-7007 (2009).
Onodera et al., "Appropriate Administration Setting and Efficacy Evaluation in Clinical Trials (Phase I to III Clinical Trials) for the Development of New Drugs," Science & Technology Co., Ltd., 1st Edition, p. 100-101.
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Parepally et al., "Brain uptake of nonsteroidal anti-inflammatory drugs: ibuprofen, flurbiprofen, and indomethacin," Pharm Res, 23(5):873-881 (2006).
Petersen et al., "Vitamin E and donepezil for the treatment of mild cognitive impairment," N Engl J Med, 352(23):2379-2388 (2005).
Pratico D: "Alzheimer's disease and non-steroidal antiinflammatory drugs: Old therapeutic tools with novel mechanisms of action?", Current Medicinal Chemistry—Central Nervous System Agents, vol. 5, No. 2, pp. 111-117, 2005.
Péhourcq et al., "Diffusion of arylpropionate non☐steroidal anti☐inflammatory drugs into the cerebrospinal fluid: a quantitative structure-activity relationship approach," Fundam Clin Pharmacol, 18(1):65-70 (2004).
Reagan-Shaw et al., "Dose Translation from Animal to Human Studies Revisited," The FASEB, 22: 659-661 (2007).
Reverchon et al., "Production of Cromolyn Sodium Microparticles for Aerosol Delivery by Supercritical Assisted Atomization," AAPS PharmSciTech 2007; 8(4) Article 114, Dec. 21, 2007.
Richards et al., "Absorption and disposition kinetics of cromolyn sodium and the influence of inhalation technique," J Pharmacol Exp Ther, 241(3):1028-1032 (1987).
Sabbagh et al., "Latrepirdine, a potential novel treatment for Alzheimer's disease and Huntington's chorea," Curr Opin Investig Drugs, 11(1): 80-91 (2010).
Schnabel, J. "Early Results of Alzheimer's Passive Vaccine Trial Mixed," Jun. 19, 2008, http://www.dana.org/News/Details.aspx?id=42815 printed Jan. 19, 2017, pp. 1-3.
Schneider et al., "Current Alzheimer's disease clinical trials: methods and placebo outcomes," Alzheimers Dement, 5(5):388-397 (2009).
Shin et al., "Interpretation of Animal Dose and Human Equivalent Dose for Drug Development," Journal of Korean Oriental Medicine, 31: 1-7 (2010).
STN database CAS RN: 16110-51-3 (Nov. 16, 1984).
Strejan et al., "Suppression of chronic-relapsing experimental allergic encephalomyelitis in strain-13 guinea pigs by administration of liposome-associated myelin basic protein," J Neuroimmunol, 7(1):27-41 (1984).
Sun et al., "Mast cells promote atherosclerosis by releasing proinflammatory cytokines," Nat Med, 13(6):719-724 (2007).
Sun et al., "Synthesis of scyllo-inositol derivatives and their effects on amyloid beta peptide aggregation," Bioorganic & Medicinal Chemistry 16 (2008), pp. 7177-7184.
Thal et al., "A randomized, double-blind, study of rofecoxib in patients with mild cognitive impairment," Neuropsychopharmacology, 30:1204-1215 (2005).
Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al, "Therapy of Alzheimer's disease: An update," African Journal of Pharmacy and Pharmacology, vol. 4(6), pp. 408-421, Jun. 2010.
Veld et al., "Nonsteroidal antiinflammatory drugs and the risk of Alzheimer's disease," N Engl J Med, 345:1515-1521 (2001).
Wang et al. "Allopregnanolone reverses neurogenic and cognitive deficits in mouse model of Alzheimer's disease," PNAS, 107(14): 6498-6503 (2010).
Weggen et al., "A subset of NSAIDs lower amyloidogenic Abeta42 independently of cyclooxygenase activity," Nature, 414(6860):212-216 (2001).
Wettstein et al., "Clinical trials with the cholinergic drug RS 86 in Alzheimer's disease (AD) and senile dementia of the Alzheimer type (SDAT)," Psychopharmacology, 84(4):572-573 (1985).
Yan et al., "Anti-inflammatory drug therapy alters β-amyloid processing and deposition in an animal model of Alzheimer's disease," J Neurosci, 23:7504-7509 (2003).
Zhang et al., "Cromolyn Reduces Levels of the Alzheimer's Disease-Associated Amyloid β-Protein by Promoting Microglial Phagocytosis," Sci Rep, 8: Article No. 1144 (2018).
Zhou et al., "Drug-lactose binding aspects in adhesive mixtures: controlling performance in dry powder inhaler formulations by altering lactose carrier surfaces," Adv Drug Deliv Rev, 64(3):275-284 (2012).
Zlokovic et al., "Neurovascular pathways to neurodegeneration in Alzheimer's disease and other disorders," Nat Rev Neurosci, 12(12):723-738 (2011).
Panza et al., "Immunotherapy for Alzheimer's Disease: From anit-b-amyloid to tau-based Immunization strategies," Immunotherapy, 4(2):213-238 (2012).
Bodor et al., "Improved delivery through biological membranes VII. Dermal delivery of cromoglycic acid (cromolyn) via its prodrugs," International Journal of Pharmaceutics, 7(1):63-75 (1980).
European Search Report for EP Application No. 13848340 dated Feb. 11, 2016.
International Search Report and Written Opinion for International Application No. PCT/US16/63143 dated Feb. 6, 2017.
International Search Report and Written Opinion for International Application No. PCT/US16/63462 dated Feb. 1, 2017.
International Search Report and Written Opinion for International Application No. PCT/US17/65727 dated Feb. 12, 2018.
Koo et al., "Amyloid diseases: Abnormal protein aggregation in neurodegeneration, " PNAS, 96:9989-9990 (1999).
Obici et al., "AA amyloidosis: basic knowledge, unmet needs and future treatments, " Swiss Medical Weekly, 142:w13580 (2012).
Tavemi et al., "Donepezil medicated memory improvement in traumatic brain injury during post acute rehabilitation, " Brain Inj, 12(1):77-80 (1998).

\* cited by examiner

CROMOLYN DERIVATIVES AND RELATED METHODS OF IMAGING AND TREATMENT

CROSS-REFERENCE TO RELATED APPLICATIONS

This application is a continuation application of U.S. application Ser. No. 14/059,924, filed Oct. 22, 2013, which is a continuation-in-part application of U.S. application Ser. No. 13/146,842 filed Nov. 16, 2011, now U.S. Pat. No. 8,617,517, issued on Aug. 5, 2010, which represents the U.S. National Stage of PCT/US2010/22495, filed Jan. 29, 2010, which claims benefit of U.S. Provisional application 61/148,245, filed Jan. 29, 2009, the contents of each of which are expressly incorporated by reference in their entirety.

STATEMENT REGARDING FEDERALLY SPONSORED RESEARCH OR DEVELOPMENT

Not Applicable.

FIELD OF THE INVENTION

The invention relates generally to medical imaging and disease treatment. In particular, the invention is directed to cromolyn derivatives for use in positron emission tomography (PET) imaging and related methods of diagnosis and therapeutic treatment.

BACKGROUND OF THE INVENTION

Coronary artery disease is the leading cause of morbidity and mortality in the United States and in most developed countries. Atherosclerosis and its complications such as myocardial infarction and stroke, is mainly responsible for coronary artery disease. All together, atherosclerosis accounts for at least forty-three percent of all death in the United States affecting over 60 million people (American Heart Association, 2004).

Advances in basic science indicate coronary artery disease is an inflammatory process, characterized by a long cycle of irritation, injury, healing and re-injury to artery endothelial cells. There is growing evidence that mast cells are found in the various stages of atherosclerosis, coronary inflammation and cardiac ischemia (Libby 2002; Fernex, 1968; Mor and Mekori, 2001; Kelly, Chi, et al., 2000; Sun, Sukhova, et al., 2007; Huang, Pang, et al., 2002). Mast cells, located in connective tissue, play an important role in helping the immune system defend tissues from disease by activating the release of intracellular mediators (degranulation), as well as attracting other key players of the immune defense system to areas of the body where they are needed. In response to vascular injury, cardiac mast cells interact with lipoproteins to deliver lipids to macrophages, and to release a large variety of cytokines that affect smooth muscle cells and T lymphocytes. This process can develop into the more advanced and complex occlusive lesions, termed fibrous plaques. Other pro-inflammatory mediators released by mast cells are histamine, which can constrict the coronaries, and cytokines IL-6 and IFN-gamma, which induce degradation of the extracellular matrix and the death of smooth muscle cells in the wall of the aorta, weakening the walls and allowing it to dilate. Thus, the inflammatory response stimulates endothelial dysfunction causing migration and proliferation of smooth muscle cells that become intermixed in the area of inflammation to form fibrous plaques and complicated lesions.

Disodium cromoglicate, termed "cromolyn," is the disodium salt of cromoglicic acid. It is used as an anti-inflammatory medication. Cromolyn is described in the literature as a mast cell stabilizer since it works by preventing the release of mediators such as the vasoactive and pro-arrhythmogenic chemical histamine and cytokines from mast cells thus stabilizing inflammatory cells. Prevention of mediator release is thought to result from indirect blockade of the entry of calcium ions into the membrane of sensitized mast cells. Cromolyn has also been shown to inhibit the movement of other inflammatory cells such as neutrophils, eosinophils, and monocytes (8).

Recent studies in mice have demonstrated that systemic mast cell activation during atherogenesis leads to plaque formation (Bot, de Jager, et al., 2007). Furthermore, treatment of the animals with the mast cell stabilizer cromolyn prevented dinitrophenyl-albumin-induced plaque expansion. In another study, cardiac mast cell activation was studied in mice after stress-related coronary inflammation (Huang, Pang, et al., 2003). Activated mast cells were found adjacent to atherosclerotic vessels. In cromolyn treated mice, release of the pro-inflammatory cytokine interleukin-6 (IL-6) present in mast cells, was partially inhibited.

There is growing evidence that activated cardiac mast cells are increased in association with coronary inflammation, myocardial infarction, as well as ischemic cardiomyopathy. Moreover, mast cells can promote the formation of human atherosclerotic lesions by causing endothelial dysfunction of the heart's arteries that lead to plaque buildup. Since cromolyn targets sensitize mast cells, a labeled cromolyn analog potentially could serve as a diagnostic probe for early detection of coronary artery disease.

As can be appreciated, it would be desirable to obtain new imaging agents useful for detecting degenerative diseases in human subjects. In particular, novel imaging probes that associate with markers of inflammation such as mast cells would facilitate the early detection of inflammatory diseases such as atherosclerosis by utilizing sensitive and non-invasive approaches such as PET or MRI imaging. Such new compounds may also provide unexpected therapeutic benefits for treatment of conditions including, but not limited to, inflammation, infection, atherosclerosis and Alzheimer's Disease.

SUMMARY OF THE INVENTION

The inventors show herein the synthesis and use of new cromolyn derivatives. Accordingly, the invention provides imaging agents suitable for imaging sites of inflammatory activity, including atherosclerotic plaques in the heart, brain and carotid artery, and β-amyloid plaques in the brain. In addition, the invention provides compounds that provide therapeutic effects in the treatment of various conditions including, but not limited to, inflammation, infection, atherosclerotic plaque, and Alzheimer's Disease.

In a first aspect, the invention provides a compound having the formula:

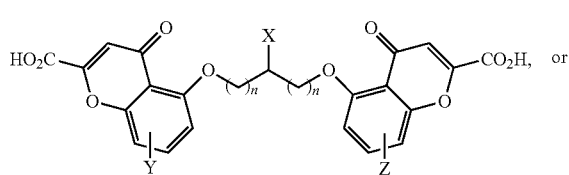

(I)

-continued

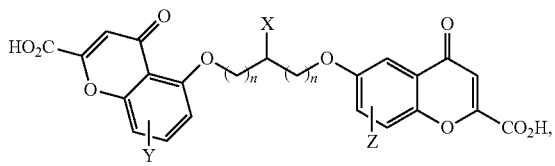

(II)

or an ester or salt of (I) or (II); wherein: X is OH, $C_1$-$C_6$ alkoxyl, Y and Z are independently selected from a $C_1$-$C_6$ alkyl, $C_1$-$C_6$ alkoxyl, halogen, un-substituted or $C_1$-$C_6$ substituted amine, $^{18}F$, $^{19}F$, or H; and n is 1, 2, or 3; and wherein for structure (I), if n are both 1 and Y and Z are both H, X is OH.

In certain embodiments, X is $^{18}F$ or $^{19}F$ and, more preferably, Y and Z are hydrogen. A particularly preferred compound has the structure:

(Compound A)

or is a salt or ester thereof.

In another embodiment, at least one of Y and Z is $^{18}F$ or $^{19}F$ and, more preferably, X is OH. Particularly preferred compounds have the structures:

or are corresponding salts or esters thereof.

In an alternative embodiment, the compound lacks a radiolabel and, preferably, X is OH and Y and Z are hydrogen, except that in such an embodiment comprising structure (I) wherein X is OH and Y and Z are hydrogen, both n cannot be 1.

Preferred compounds of the invention, particularly for imaging purposes, localize to atherosclerotic plaques in the heart, brain and/or carotid artery of a subject, or to β-amyloid plaques in the brain of a subject.

In another aspect, the compounds of the invention are provided in the form of a pharmaceutically appropriate dosage of one or more of the compounds described and claimed herein formulated with a pharmaceutically acceptable carrier.

As can be appreciated, the compounds of the invention are useful for imaging in other modalities in addition to PET imaging. Exemplary compounds may be optionally isotopically labeled with isotopes such as the $^{19}F$ isotope, or $^{13}C$ isotope to facilitate nuclear magnetic resonance imaging (MM).

In yet another aspect of the invention, a method for providing a positron emission tomography (PET) scan of a subject is provided. Such a method includes steps of: (a) administering to a subject a compound containing an $^{18}F$ label as described and claimed herein; and (b) imaging gamma rays emitted due to the compound within the subject in order to provide a PET scan of the compound contained in the subject.

In preferred methods, the presence, absence or level of the compound within the subject is indicative of a disease state including, but not limited to, atherosclerotic plaque alternatively present in the heart, brain, or carotid artery of the subject.

The subject is preferably a living animal, most preferably a human.

The compound is typically administered to the subject via intravenous (IV) injection.

In certain alternative methods, an additional step of contrast imaging the subject by magnetic resonance imaging (MM) or x-ray computed tomography (CT) is included.

In yet another embodiment, the invention provides a method for providing a magnetic resonance image of a subject. Such a method includes steps of: (a) administering to a subject a compound containing an $^{18}F$ label according to the present invention; and (b) imaging the subject in order to obtain a magnetic resonance image of the compound contained within the subject.

The presence, absence or level of the compound within the subject is indicative of a disease state, preferably atherosclerotic plaque present in the heart, brain, or carotid artery of the subject.

The invention further encompasses treatment methods, including treatment of atherosclerotic plaque in a subject. Such a method includes steps of administering to a subject an effective dosage of a compound of the invention, whereby the atherosclerotic plaque is treated in the subject.

In an alternative method, the invention provides a method of treating Alzheimer's Disease in a subject including the steps of administering to a subject an effective dosage of an inventive compound, whereby Alzheimer's Disease is treated in the subject.

Also provided by the invention are novel methods of efficiently preparing fluorinated compounds. Such methods provide for quicker synthesis and purification than is seen in conventional methods. Accordingly, the methods are particularly suited for fluorinating compounds with radiolabeled fluorine for use in imaging applications.

In some embodiments of a method of preparation, a fluoride moiety is contacted with an organic compound having a triflate or tosylate moiety on an aliphatic carbon atom under anhydrous or aprotic conditions. Under such conditions, the fluoride moiety acts as a nucleophile and the triflate or tosylate acts as a leaving group in a nucleophilic substitution reaction, resulting in the fluorination of the organic compound. Preferably, the fluoride moiety used in the method is F-18.

In certain such embodiments, the organic compound contacted with the fluoride moiety is 1,3-bis[(tolylsulfonyl)oxy]-2-[(trifluoromethyl)sulfonyl]oxy-propane, and the resulting product is further reacted with other compounds to provide a fluorinated cromolyn derivative. In one embodiment, cromolyn derivatives are provided wherein X in structure (I) or structure (II) above is a fluorine atom. Preferably, the fluorine atom is radiolabeled F-18.

In yet other embodiments of a method of preparation, a fluoride moiety is contacted under anhydrous or aprotic conditions with an organic compound having an activated aromatic ring wherein the aromatic ring is linked to a nitro group, a substituted ammonium ion, a substituted sulphonium ion, a substituted phosphonium ion, or a halogen. Under such conditions, the fluoride moiety exchanges for the nitro group, substituted ammonium ion, substituted sulphonium ion, substituted phosphonium ion, or halogen, resulting in the fluorination of the organic compound on the aromatic ring. Preferably, the fluoride moiety used in the method is F-18.

In certain such embodiments, the organic compound contacted with the fluoride moiety is a cromolyn derivative-based substituted ammonium salt wherein the nitrogen atom of the substituted ammonium ion is attached to an aromatic ring of the chromolyn derivative. In some such embodiments, cromolyn derivatives are provided wherein Y or Z in structure (I) or structure (II) above is a fluorine atom. Preferably, the fluorine atom is radiolabeled F-18.

Of course, the invention also contemplates the use of a compound as described and claimed herein for the manufacture of an injectable dosage for the in vivo imaging of a subject as well as a medicament for the treatment of disease conditions such as atherosclerotic plaque and Alzheimer's Disease. In addition, the invention encompasses the use of the present compounds in in vivo imaging of a subject and treatment of disease conditions.

In one embodiment, the present invention is a method for treating Alzheimer's Disease in a subject comprising the step of administering by systemic delivery an effective amount of a compound having the formula:

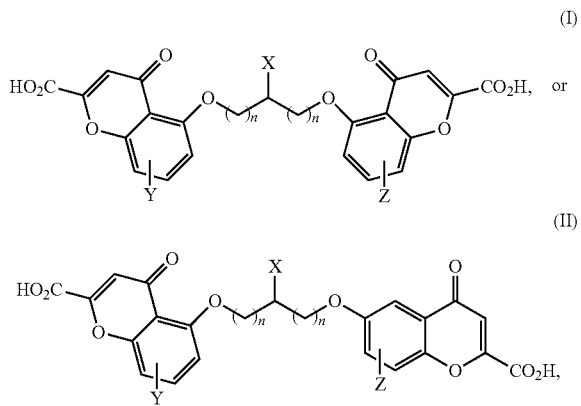

or a salt or ester of (I) or (II); wherein: X is OH, $C_1$-$C_6$ alkoxyl, Y and Z are independently selected from a $C_1$-$C_6$ alkyl, $C_1$-$C_6$ alkoxyl, halogen, un-substituted or $C_1$-$C_6$ substituted amine, $^{18}F$, $^{19}F$, or H; and n is 1, 2, or 3, wherein Alzheimer's Disease is treated in the subject.

In another embodiment, the present invention is a method for inhibiting the polymerization of amyloid-beta peptide oligomers in a subject comprising the step of administering by systemic delivery an effective amount of a compound having the formula:

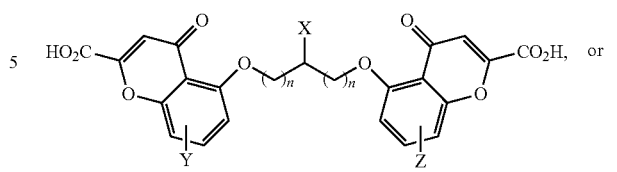

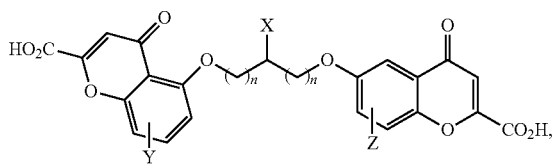

or a salt or ester of (I) or (II); wherein: X is OH, Y and Z are independently selected from a $C_1$-$C_6$ alkyl, $C_1$-$C_6$ alkoxyl, halogen, un-substituted or $C_1$-$C_6$ substituted amine, $^{18}F$, $^{19}F$, or H; and n is 1, 2, or 3, wherein the polymerization of amyloid-beta peptide oligomers in the subject is inhibited.

Other objects, features and advantages of the present invention will become apparent after review of the specification, claims and drawings.

BRIEF DESCRIPTION OF THE DRAWINGS

FIG. 2A shows that Aβ-40 level decreases following by treatment of cromolyn sodium with dose-dependency. FIG. 2B shows that Aβ-42 level decreases following by treatment of cromolyn sodium with dose-dependency. N=3 or 5 animals per group, average±SE. The p value is significant using one-way ANOVA test (Bonferroni's test). Both of total soluble Aβ (as shown as Gdn+) and monomeric Aβ (as shown as Gdn−) decease after the addition of cromolyn sodium. The dose of 2.1 mg/kg of cromolyn sodium was enough to decrease TBS soluble Aβ.

FIG. 3A shows the experiments of IBL Aβ oligomer ELISA (82E1-82E1). FIGS. 3B and 3C show the difference the experiments with Gdn and those without Gdn using Aβ WAKO ELISA. N=3 or 5 animals per group, average±SE. The p value is not significant using one-way ANOVA test (Bonferroni's test). Both ELISA (IBL oligomer ELISA and the differences between with and without Gdn using WAKO ELISA) showed that oligomer level was not changed following the treatment with cromolyn sodium.

FIG. 5 illustrates Aβ aggregation test in the absence of cromolyn. The experiment was assayed by thioflavin fluorescent intensity kinetics.

DETAILED DESCRIPTION OF THE INVENTION

I. In General

Figure 1:
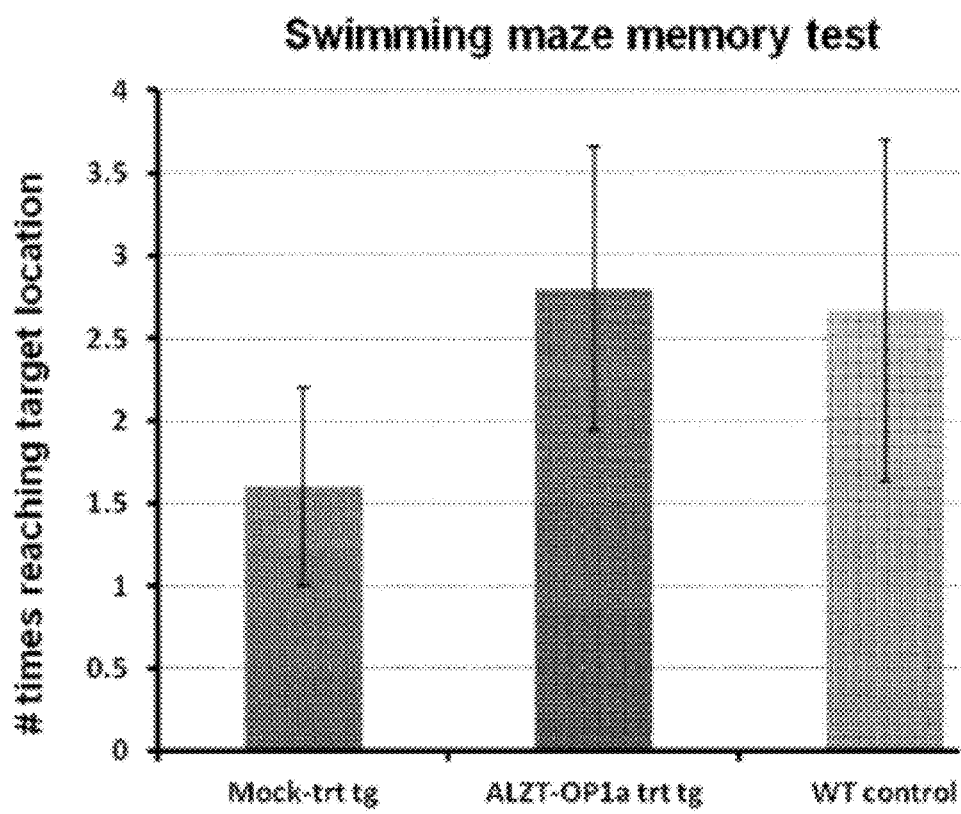
FIG. 1 illustrates the water maze recorded data of in vivo cromolyn and ibuprofen treatment of transgenic mice-modeling like Alzheimer's Disease. The results indicate that treated transgenic mice have closely behavior to wild type normal control group.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terminology as set forth herein is for description of the embodiments only and should not be construed as limiting of the invention as a whole. Unless otherwise specified, "a," "an," "the," and "at least one" are used interchangeably and mean one or more than one.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for cromolyn derivatives of this invention are those that do not interfere with the cromolyn derivatives imaging activity. In the context of the present invention, the term "aliphatic group" means a saturated or unsaturated linear or branched hydrocarbon group. This term is used to encompass alkyl, alkenyl, and alkynyl groups, for example.

The terms "hydroxy" and "hydroxyl" refer to the group —OH.

The term "oxo" refers to the group =O.

The term "carboxylate" or "carboxyl" refers to the group —COO⁻ or —COOH.

The term "cyano" refers to the group —CN.

The term "nitro" refers to the group —NO$_2$.

The term "amino" refers to the group —NH$_2$.

The term "acyl" or "aldehyde" refers to the group —C(=O)H.

The term "amido" or "amide" refers to the group —C(O)NH$_2$.

The term "aminoacyl" or "acylamino" refers to the group —NHC(O)H.

The term "thiol" refers to the group —SH.

The term "thioxo" refers to the group =S.

The term "sulfinyl" refers to the group —S(=O)H.

The term "sulfonyl" refers to the group —SO$_2$H.

The term "sulfonylamido" or "sulfonamide" refers to the group —SO$_2$NH$_2$.

The term "sulfonate" refers to the group SO$_3$H and includes groups having the hydrogen replaced with, for example a C$_{1-6}$alkyl group ("alkylsulfonate"), an aryl ("arylsulfonate"), an aralkyl ("aralkylsulfonate") and so on. C$_{1-3}$sulfonates are preferred, such as for example, SO$_3$Me, SO$_3$Et and SO$_3$Pr.

The term "isomers", as used herein, refer to stereoisomers, diastereomers, enantiomers and tautomers. "Tautomers" may be isomers that are readily interconvertable by rapid equilibrium. For example, carbonyl compounds that have a hydrogen on their alpha-carbon are rapidly interconverted with their corresponding enols.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. "Halogens" are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)NR$_2$ each of the two R groups is independently selected.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "therapeutically effective amount" or "pharmaceutically appropriate dosage", as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration", as used herein, refers to providing the compound or pharmaceutical composition of the invention to a subject suffering from or at risk of the diseases or conditions to be treated or prevented.

The term "systemic delivery", as used herein, refers to any suitable administration methods which may delivery the compounds in the present invention systemically. In one embodiment, systemic delivery may be selected from the group consisting of oral, parenteral, intranasal, inhaler, sublingual, rectal, and transdermal administrations.

A route of administration in pharmacology and toxicology is the path by which a drug, fluid, poison, or other substance is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

The examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

The examples for parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

Any route of administration may be suitable for the present invention. In one embodiment, the compound of the present invention may be administered to the subject via intravenous injection. In another embodiment, the compounds of the present invention may be administered to the subject via any other suitable systemic deliveries, such as oral, parenteral, intranasal, sublingual, rectal, or transdermal administrations.

In another embodiment, the compounds of the present invention may be administered to the subject via nasal systems or mouth through, e.g., inhalation.

In another embodiment, the compounds of the present invention may be administered to the subject via intraperitoneal injection or IP injection.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

In animals, IP injection is used predominantly in veterinary medicine and animal testing for the administration of systemic drugs and fluids due to the ease of administration compared with other parenteral methods.

In humans, the method of IP injection is widely used to administer chemotherapy drugs to treat some cancers, in particular ovarian cancer. Although controversial, this specific use has been recommended as a standard of care.

II. The Invention

In certain aspects, the invention is directed to radiolabeled cromolyn analogs for medical imaging of inflammatory sites such as atherosclerotic plaques in the heart, brain, or carotid artery of a subject. In other aspects, the present compounds, in radiolabeled or unlabeled form, are treatment agents for various disease conditions including, e.g., atherosclerotic plaques and Alzheimer's Disease.

Disodium cromoglicate, or sometimes called cromolyn, is an anti-inflammatory medication. Cromolyn is understood to be a mast cell stabilizer and apparently works by preventing the release of mediators such as the vasoactive and proarrhythmogenic chemical histamine and cytokines from mast cells thus stabilizing inflammatory cells. Prevention of mediator release is thought to result from indirect blockade of the entry of calcium ions into the membrane of sensitized mast cells. Cromolyn has also been shown to inhibit the movement of other inflammatory cells such as neutrophils, eosinophils, and monocytes. The present inventors describe herein the manufacture and use of new analogs and new radiolabeled analogs of cromolyn for use as potential agents for treatment, imaging and as biomarkers for following progression, treatment efficacy and prevention of atherosclerosis and β-amyloid plaque formation. In certain embodiments, cromolyn analogs are radiolabeled with nuclides that allow PET and MRI imaging. The invention further provides methods for the preparation and use of the compounds for targeting and treating active infection and other inflammatory processes, such as atherosclerosis or, alternatively, Alzheimer's Disease.

As can be appreciated, the compounds of the present invention may be used for several purposes. For instance, the described compounds are a potential research tool for animal studies; a diagnosis agent for clinicians; a biomarker for biology studies; a potential class of drugs to treat atherosclerosis or Alzheimer's Disease; a MM imaging probe for atherosclerosis or Alzheimer's (e.g., a compound containing at least one fluorine atom which is an $^{19}$F isotope); and a PET probe for atherosclerosis or Alzheimer's diagnosis (e.g., a compound containing at least one fluorine atom which is an $^{18}$F isotope or, alternatively, at least one carbon atom which is a $^{13}$C isotope).

Cromolyn derivatives are expected to be beneficial for use in the imaging methods of the invention. As used herein, the term "cromolyn derivative" is used interchangeably with the term "cromolyn analog" and "cromolyn analogue" (alternative spelling).

Cromolyn derivatives that exhibit improved imaging qualities are preferred. Cromolyn derivatives of the invention are generally encompassed by compounds having the formula:

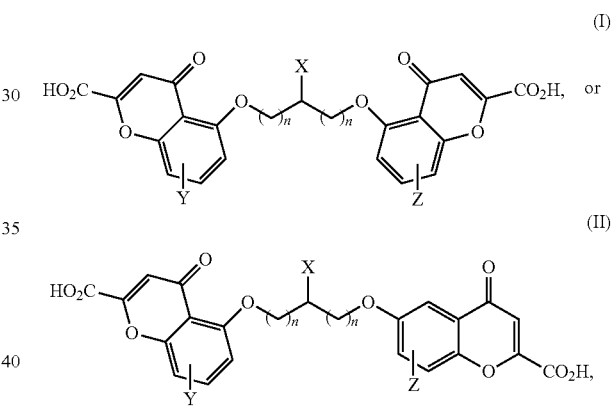

or esters or salts of (I) or (II);

wherein: X is OH, $C_1$-$C_6$ alkoxyl, $^{18}$F, or $^{19}$F; Y and Z are independently selected from a $C_1$-$C_6$ alkyl, $C_1$-$C_6$ alkoxyl, halogen, un-substituted or $C_1$-$C_6$ substituted amine, $^{18}$F, $^{19}$F, or H; and n is 1, 2, or 3; and wherein for structure (I), if n are both 1 and Y and Z are both H, X is not OH.

In certain embodiments, X is $^{18}$F or $^{19}$F and, more preferably, Y and Z are hydrogen. A particularly preferred compound has the structure:

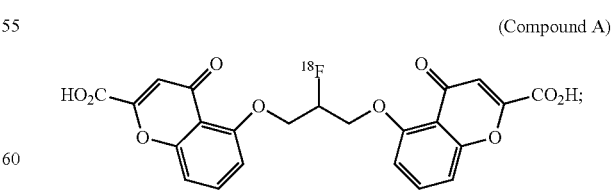

or is a salt or ester thereof.

In another embodiment, at least one of Y and Z is $^{18}$F or $^{19}$F and, more preferably, X is OH. Particularly preferred compounds have the structures:

(Compound B)

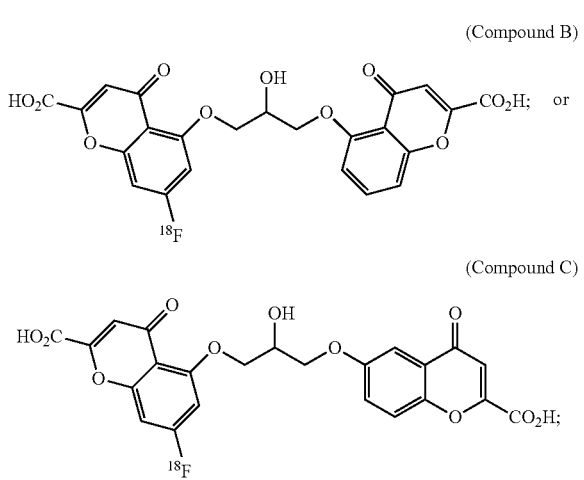

(Compound C)

corresponding esters or salts thereof.

In an alternative embodiment, the compound lacks a radiolabel and, preferably, X is OH and Y and Z are hydrogen, except that in such an embodiment comprising structure (I) wherein X is OH and Y and Z are hydrogen, both n cannot be 1.

Preferred compounds of the invention, particularly for imaging purposes, localize to atherosclerotic plaques in the heart, brain and/or carotid artery of a subject.

A preferred dosage range of the present compounds for administration to animals, including humans, is from about 0.001 mg/kg to about 500 mg/kg. Specifically, for PET and MM imaging, the preferred dosage range is from about 0.1 mg/kg to about 500 mg/kg. Based on these parameters, the artisan may perform no more than routine experimentation to optimize the dosage for a particular application.

Compounds lacking radiolabel are, of course, useful for the treatment methods claimed and disclosed herein. Specific methods to synthesize exemplary compounds according to the invention are set forth below in the Examples section. In general, the inventors utilize novel synthetic radiofluorination approaches to provide the present compounds. Schemes I and II shown below illustrate preferred embodiments of the manufacturing processes.

Radiofluorination-Scheme I

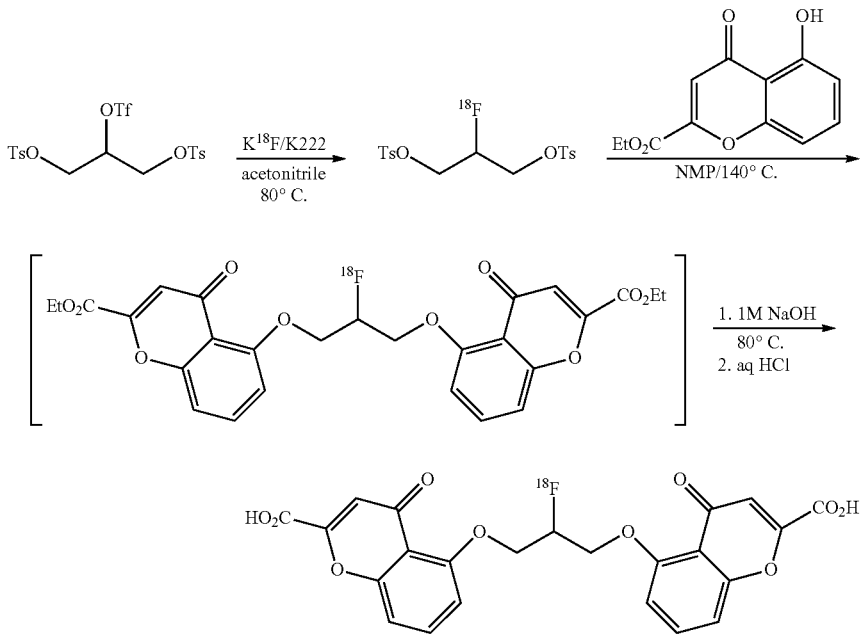

Aromatic Radiofluorination-Scheme II

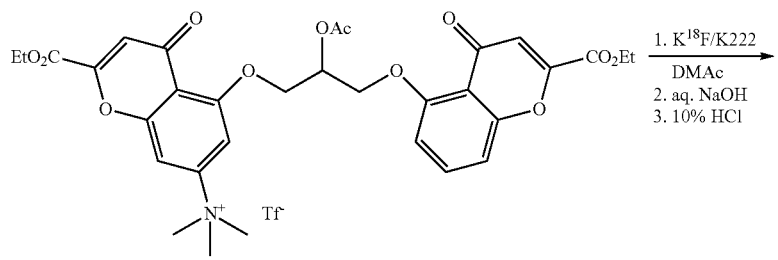

-continued

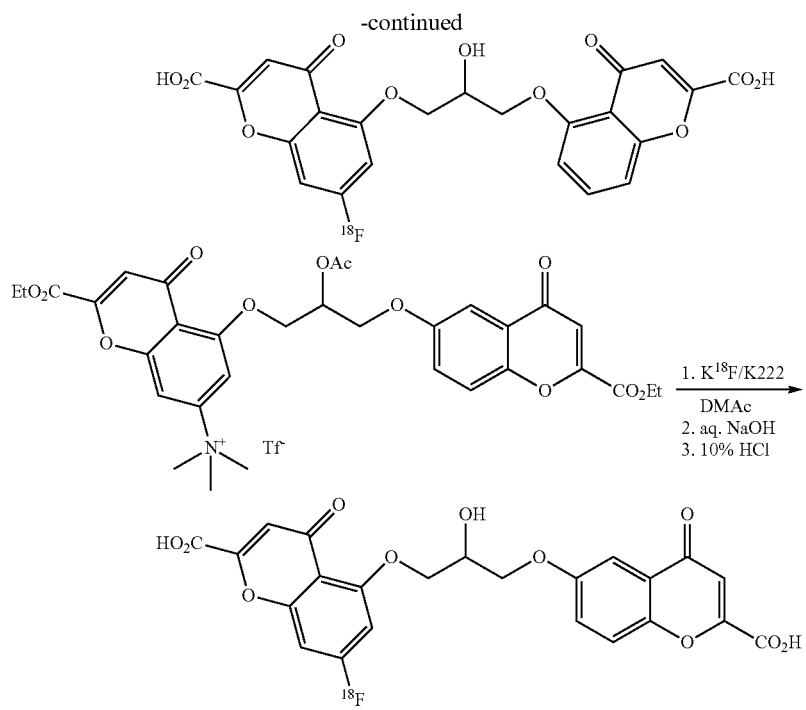

In certain embodiments directed to formulations and medicaments for disease treatment including, e.g., atherosclerosis or Alzheimer's, the inventive compounds may be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The inventive compounds further encompass esters of the described compounds, wherein the acidic hydrogen on one or more of the acidic moieties is substituted by an alkyl group.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The compounds of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The compounds according to the present invention are anticipated to act as treatment agents for inflammation, particularly atherosclerotic plaques, as can be demonstrated by standard protocols commonly known in the field. Accordingly, another aspect of the invention provides a method for treating atherosclerotic plaque in a subject, comprising administering to a subject an effective dosage of a compound according to the present invention, whereby the atherosclerotic plaque is treated in the subject. In the treatment of atherosclerotic plaque, suitable dosage level (i.e., an effective amount) is from about 0.001 mg/kg to about 500 mg/kg per day, preferably about 1 mg/kg per day. The compounds may be administered on a regimen of 1 to 4 times per day, or on a continuous basis.

In one embodiment, the present invention is a method for treating Alzheimer's disease in a subject comprising the step of administering by systemic delivery an effective amount of a compound having the formula:

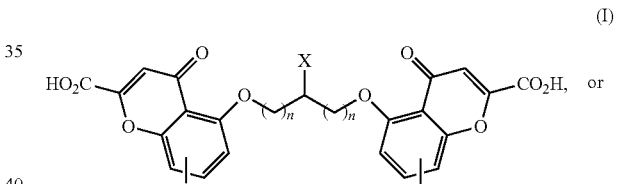

(I)

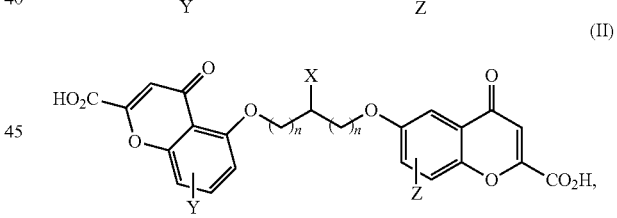

(II)

or a salt or ester of (I) or (II);

wherein: X is OH, $C_1$-$C_6$ alkoxyl;

Y and Z are independently selected from a $C_1$-$C_6$ alkyl, $C_1$-$C_6$ alkoxyl, halogen, un-substituted or $C_1$-$C_6$ substituted amine, $^{18}F$, $^{19}F$, or H; and n is 1, 2, or 3, wherein Alzheimer's Disease is treated in the subject.

In one specific embodiment, the method of administering by systemic delivery is selected from the group consisting of oral, parenteral, intranasal, sublingual, rectal, and transdermal administration.

In another embodiment, the present invention is a method for inhibiting the polymerization of amyloid-beta peptide oligomers in a subject comprising the step of administering by systemic delivery an effective amount of a compound having the formula:

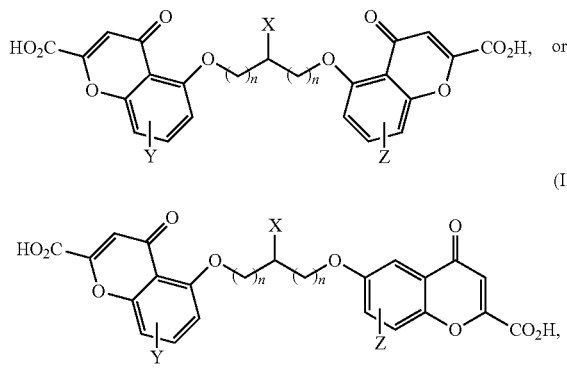

or a salt or ester of (I) or (II);
wherein: X is OH;
Y and Z are independently selected from a $C_1$-$C_6$ alkyl, $C_1$-$C_6$ alkoxyl, halogen, un-substituted or $C_1$-$C_6$ substituted amine, $^{18}F$, $^{19}F$, or H; and
n is 1, 2, or 3, wherein the polymerization of amyloid-beta peptide oligomers in the subject is inhibited.

In one specific embodiment, the method of administering by systemic delivery is selected from the group consisting of oral, parenteral, intranasal, sublingual, rectal, and transdermal administration.

In another specific embodiment, the method of inhibiting the polymerization of amyloid-beta peptide oligomers comprises treating Alzheimer's disease in the subject.

The Example describes the use of cromolyn and its derivatives for inhibiting polymerization of Alzheimer's Disease oligomers and thus treating Alzheimer's Disease.

The compounds according to the present invention are anticipated to act as treatment agents for Alzheimer's Disease, as can be demonstrated by standard protocols commonly known in the field. Accordingly, another aspect of the invention provides a method for treating Alzheimer's Disease in a subject, comprising administering to a subject an effective dosage of a compound of the invention, whereby Alzheimer's Disease is treated in the subject. In the treatment of Alzheimer's Disease, suitable dosage level (i.e., an effective amount) is from about 0.001 mg/kg to about 500 mg/kg per day, preferably about 0.1 mg/kg to about 50 mg/kg per day, more preferably about 1-10 mg/kg per day. The compounds may be administered on a regimen of 1 to 4 times per day, or on a continuous basis.

In another embodiment, an appropriate dosage level for the present invention may generally be about 0.001 to about 500 mg per kg subject body weight per day which can be administered in a single or multiple doses. Preferably, the dosage level will be about 0.01 to about 250 mg/kg per day; more preferably about 0.05 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage may be about 0.05 to about 0.5, about 0.5 to about 5 or about 5 to about 50 mg/kg per day. The dosage may be selected, for example, to include any dose within any of these ranges, for therapeutic efficacy and/or symptomatic adjustment of the dosage to the subject to be treated.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Synthesis of F-18 Labeled Cromolyn
Radiofluorination.

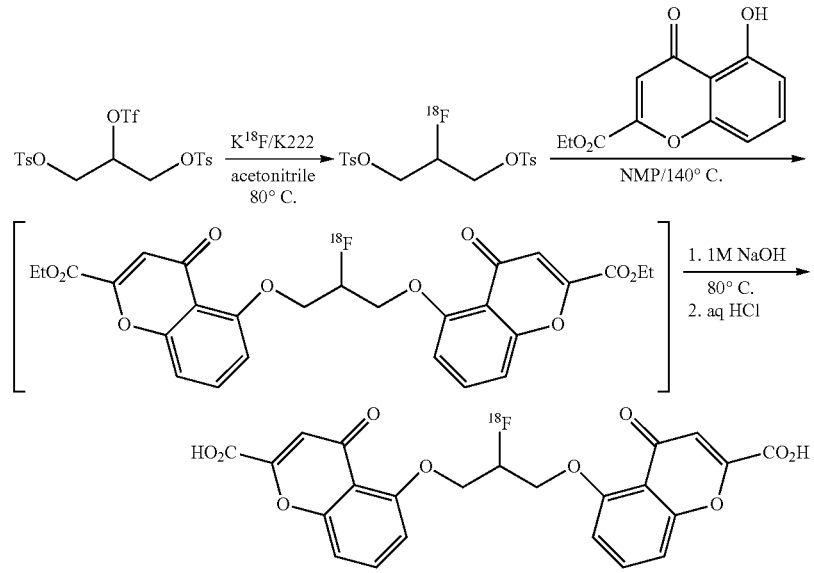

5,5'-(2-[18F]fluoropropane-1,3-diyl)bis(oxy)bis(4-oxo-4H-chromene-2-carboxylic acid)

A Wheaton 5-mL reaction vial containing 50 mCi of fluorine-18 in 1 mL of $^{18}$O-enriched water, Kryptofix-2.2.2. (6 mg), and potassium carbonate (2 mg) was heated at 120° C. and solvent was evaporated with the aid of nitrogen gas. The K$^{18}$F/Kryptofix complex was dried three times at 120° C. by the addition of 1 mL of acetonitrile followed by evaporation of the solvent using a nitrogen flow. A solution of 1,3-bis[tolylsulfonyl)oxy]-2-[(trifluoromethyl)sulfonyl]oxy-propane (4 mg) in acetonitrile was added to the vial and fluorination was performed at 80° C. for 10 min. The resultant 2-[$^{18}$F]fluoropropane 1,3-ditosylate solution (90% rxn, radioTLC) was passed through a silica gel SepPak using methylene chloride into a vial containing K$_2$CO$_3$ (10 mg) and ethyl 5-hydroxy-4-oxo-4H-chromene-2-carboxylate (10 mg). After solvent removal, N-methyl-2-pyrrolidone (NMP) was added and the mixture was heated for 20 min at 140° C. Once cooled, 1 M NaOH (100 uL) was added and the mixture was heated for 10 min at 80° C. The mixture was diluted with 1M HCl (3 mL) and passed through a C-18 SepPak. Polar materials were eluted with 1M HCl and F-18 cromolyn with 20:80 acetonitrile/PBS (1 mL). F-18 cromolyn was purified by HPLC (Phenomenex Luna C$_{18}$, 250×10 mm, gradient: 0 to 40% acetonitrile in 20 mM phosphate buffer, pH 6.5). Solvent was evaporated the activity (5 mCi, 20% EOB) was dissolved in saline and filtered (0.22µ Millex-GV). Synthesis was complete within 2 hr and chemical purity was greater than 95%.

Example 2

Synthesis of Precursors

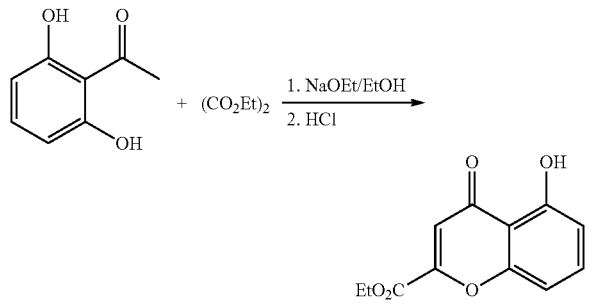

2-Carbethoxy-5-hydroxy-γ-chromone

A mixture of 2,6-dihydroxyacetophenone (1.0 g, 6.6 mmol) and ethyl oxalate (0.15 g, 6.6 mmol) in ether (10 mL) was added to a solution of sodium ethoxide (0.4 g Na, 20 mmol) in ethanol (15 mL). The mixture was stirred at 25° C. for 30 min, heated at reflux for 1.5 hr, cooled and filtered. The precipitated sodium salt was washed with ether and dried. It was then dissolved in water and acidified with 10% HCl to form a sticky solid. The solid was refluxed in ethanol (20 mL) with a catalytic amount of 36% HCL for 1 hr. The mixture was poured into 50 mL of water and extracted twice with methylene chloride (50 mL). The extracts were combined and dried. After solvent removal, the crude material was chromatographed on silica gel (ethyl acetate/hexane 20:80) to yield 0.57 g (40%) of a yellow product; mp 146-148° C. (Lit. 148° C.); $^1$H NMR (CDCl$_3$), d 1.42 (t, 3H, J=7.14 Hz, CH3), 4.47 (q, 2H, J=7.14 Hz), 6.82 (d, 2H, J=8.24 Hz, Aro-H), 7.02 (d, 2H, J=4.0 Hz, Aro-H), 7.02 (s, 1H, vinyl-H), 7.58 (t, 1H, J=8.24 Hz, Aro-H), 12.1 (s, 1H, phenol-H).

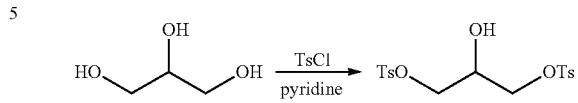

1,3-Bis(4-methylbenzenesulfonate) propanetriol

A solution of glycerol (11 g, 120 mmol) in methylene chloride (80 mL), DMAP (30 mg) and pyridine (20 mL) was treated at 0-5° C. with p-toluenesulfonyl chloride (54.6 g, 239 mmol) over a period of 30 min. The mixture was stirred at 25° C. for 16 hr, diluted with water (100 mL) and layers separated. The methylene chloride layer was washed with 1N HCl until the wash solution was acidic and then dried (sodium sulfate). After solvent removal, the crude material was chromatographed on silica gel (methanol/methylene chloride 0:100 to 5:95) to yield 14.5 g (30%) of an oil; $^1$H NMR (CDCl$_3$), δ 2.5 (s, 6H, CH3), 4.25 (m, 4H, CH2), 5.09 (m, 1H, CH), 7.4 (d, 4H, J=8.1 Hz, Aro-H), 7.78 (d, 4H, J=8.4 Hz, Aro-H).

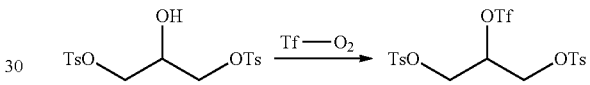

1,3-Bis(4-methylbezenesulfonate)-2-trifluoromethyl sulfonate propanetriol.

A mixture of 1,3-bis(4-methylbezenesulfonate) propanetriol 100 mg (0.25 mmol) in methylene chloride (20 mL) and pyridine (1 mL) at 0-5° C. was treated with trifluoromethanesulfonic anhydride (141 mg, 0.50 mmol). The mixture was stirred at 0-5° C. for 1 hr and then allowed to warm to 25° C. and stirred for 4 hr. The mixture was diluted with water (30 mL) and layers separated. The methylene chloride layer was washed with 1N HCl until the wash solution was acidic and then dried (sodium sulfate). After solvent removal, the crude material was chromatographed on silica gel (methylene chloride) to yield 66 mg (50%) of a solid; mp 145-147° C.; $^1$H NMR (CDCl$_3$), δ 2.5 (s, 6H, CH3), 4.25 (d, 4H, J=4.6 Hz, CH2, 5.09 (m, 1H, CH), 7.4 (d, 4H, J=8.1 Hz, Aro-H), 7.78 (d, 4H, J=8.4 Hz, Aro-H).

3-Bis(4-methylbezenesulfonate)-2-fluoropropanediol

A solution of 1,3-bis(4-methylbezenesulfonate) propanetriol (2.7 g, 6.78 mmol) in methylene chloride (20 mL) at 0-5° C. was treated with DAST (2.18 g, 13.6 mmol). The mixture was stirred at 0-5° C. for 30 then allowed to warm to 25 and stirred for 16 hr. The mixture was poured into a sat'd sodium bicarbonate solution (30 mL) and layers separated. The methylene chloride layer dried (sodium sulfate). After solvent removal, the crude material was chromatographed on silica gel (methylene chloride) to yield 0.82 g (30%) of a solid; mp 99-102° C.; $^1$H NMR (CDCl$_3$), δ 2.5

(s, 6H, CH3), 4.15 (dd, 4H, J=12.3, 4.6 Hz, CH2, 4.8 (dq, 1H, J=47, 4.6, CHF), 7.45 (d, 4H, J=8.1 Hz, Aro-H), 7.75 (d, 4H, J=8.4 Hz, Aro-H).

Example 3

Synthesis of Standard 5,5'-(2-fluoropropane-1,3-diyl)bis(oxy)bis(4-oxo-4H-chromene-2-carboxylic acid)

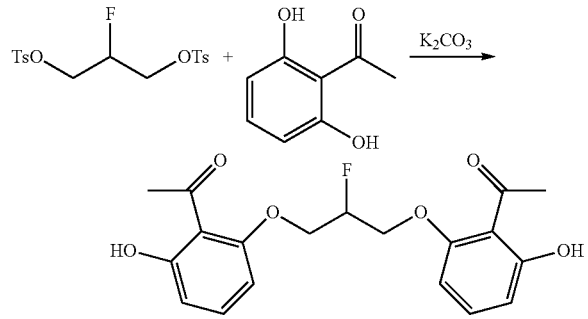

1,3-Bis(2-acetyl-3-hydroxyphenoxy)-2-fluoropropane

A mixture of 3-bis(4-methylbezenesulfonate)-2-fluoro-propanediol (1.0, 2.5 mmol), 2,6-dihydroxyacetophenone (0.76 g, 5.0 mmol) and potassium carbonate (0.69 g) in acetonitrile (40 mL) was heated under reflux for 16 hr. The mixture was filtered and the filtrate was evaporated. The crude material was chromatographed on silica gel (acetonitrile/methylene chloride 5:95) to yield 0.57 g (40%) of product; mp 162-165° C.; ¹H NMR (d6-DMSO), δ 2.5 (s, 6H, 2CH3), 4.38 (m, 4H, 2CH2), 5.22 (br d 1H, J=49 Hz, CHF), 6.45 (m, 4H, 4Aro-H), 7.28 (t, 2H, J=4.55 Hz, 2Aro-H).

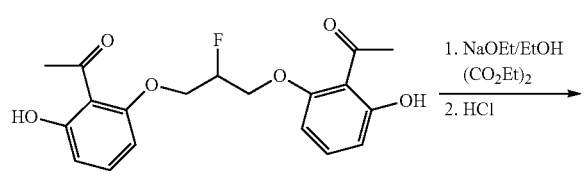

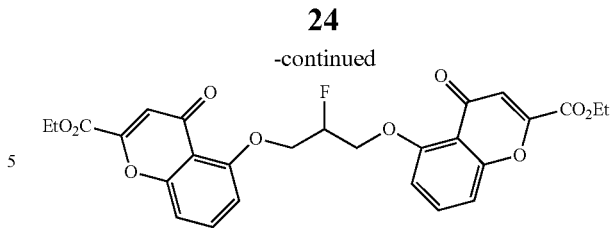

1,3-Bis(2-carboxychromon-5-yloxy)-2-fluoropropane diethyl ester

A mixture of 1,3-bis(2-acety-3-hydroxyphenoxy)-2-fluoropropane (200 mg, 0.52 mmol) and ethyl oxalate (2 mL) was added to a solution of sodium ethoxide (87 mg Na) in ethanol (10 mL) and benzene (10 mL). The mixture was heated at reflux for 16 hr, cooled and diluted with ether (50 mL). The precipitated sodium salt was filtered, washed with ether and dried. It was then dissolved in water and acidified with 10% HCl to obtain a sticky solid. The solid was refluxed in ethanol (20 mL) with a catalytic amount of 36% HCL for 1 hr. The mixture was poured into 50 mL of water and extracted twice with methylene chloride (50 mL). The extracts were combined and dried. After solvent removal, the crude material was chromatographed on silica gel (acetonitrile/methylene chloride 10:90) to yield 0.12 g (45%) of a white product; mp 166-170° C.; ¹H NMR (CDCl₃), d 1.42 (t, 6H, J=7.14 Hz, 2CH3), 4.58 (q, 4H, J=7.14 Hz 2CH2), 4.65 (m, 4H, 2CH2), 5.35 (dq, 1H, J=46 Hz, J=4.4 HZ, CHF), 6.90 (s, 2H, vinyl-H), 6.95 (d, 2H, J=8.24 Hz, 2Aro-H), 7.13 (d, 2H, J=8.24 Hz, 2Aro-H) 7.6 (t, 2H, J=8.24 2Aro-H).

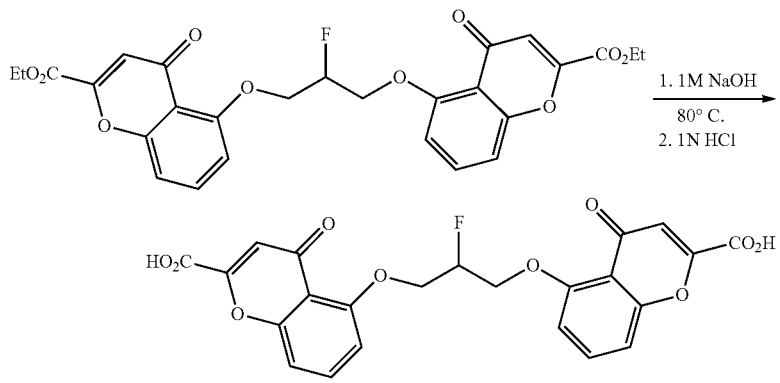

5,5'-(2-fluoropropane-1,3-diyl)bis(oxy)bis(4-oxo-4H-chromene-2-carboxylic acid)

A suspension of 1,3-bis(2-carboxychromon-5-yloxy)-2-fluoropropane diethyl ester (100 mg, 0.19 mmol) in methanol (20 mL) and 1 M sodium hydroxide (2 mL) was heated at 80 C for 1 hr. The solution was acidified with 10% HCl and volatiles were removed. A solution of methanol/methylene chloride (50:50) was added to the solid and the mixture was filtered. Evaporation afforded 76 mg (85%) of product; ¹H NMR (d6-DMSO), δ 4.65 (m, 4H, 2CH2), 5.32 (br d, 1H, J=46 Hz, CHF), 6.80 (s, 2H, 2vinyl-H), 7.2 (d, 2H, J=8.24 Hz, 2Aro-H), 7.71 (t, 2H, J=8.24 2Aro-H).

Example 4

Biodistribution

Biodistribution of F-18 cromolyn (Compound A) was performed in normal mice at 5, 30 and 60 min after intravenous injection into the tail vein (50 uCi per animal). At 5 min, organ activity (DPG) was: heart: 1.09%, blood: 3.3%, lung: 1.90%, liver: 7.69%, and brain: 0.15%. At 30 and 60 min, washout of activity was seen in all organs. Heart uptake was decreased from 1.09% to 0.18%. The data is provided in Table 1 below and in bar graph format in FIG. 4.

TABLE 1

F-18 Cromolyn Tissue Distribution (% Dose/gram) in Normal Mice

| Organ | 5 min | 30 min | 60 min |
|---|---|---|---|
| blood | 3.31 ± 1.37 | 0.92 ± 0.20 | 0.44 ± 0.15 |
| heart | 1.09 ± 0.13 | 0.32 ± 0.03 | 0.18 ± 0.07 |
| lung | 1.90 ± 1.04 | 0.62 ± 0.19 | 0.29 ± 0.21 |
| liver | 7.69 ± 0.41 | 3.11 ± 0.36 | 1.76 ± 0.74 |
| brain | 0.15 ± 0.37 | 0.04 ± 0.007 | 0.03 ± 0.004 |

Standard deviation (±)

Example 5

Aromatic Radiofluorination

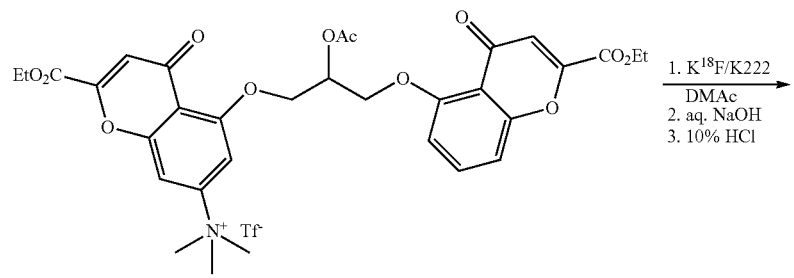

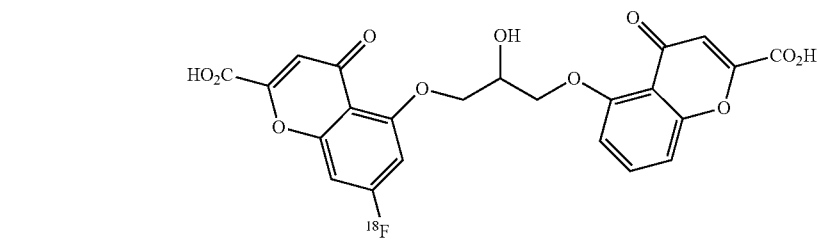

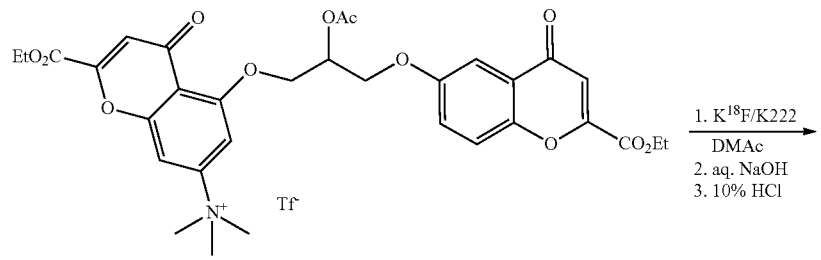

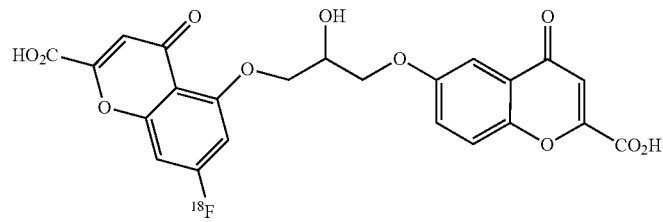

Radiofluorination of cromolyn N,N,N-trimethylbenzenaminium triflate is done in a sealed vial containing dry K[18]F/Kryptofix in dimethylacetamide (DMAc) for 5 min at 140° C. The resultant F-18 cromolyn solution is diluted with water and passed through a C-18 SepPak. Polar materials are eluted with water and product eluted with methanol into a vial. A solution of 1N sodium hydroxide is added and the vial is heated for 10 min at 80° C. The mixture is acidified and F-18 cromolyn is purified by HPLC.

Alternative Route:

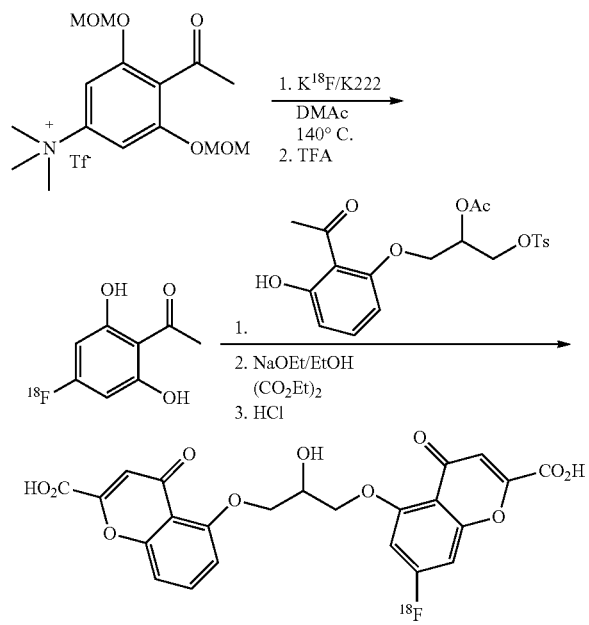

Example 6

Synthesis of Precursors

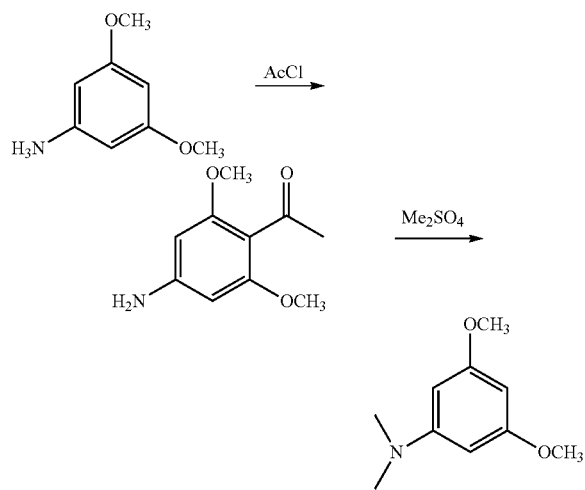

1-(4-Amino-2,6-dimethoxyacetophenone) [Dillon, Michael Patrick; Jahangir, Alam; Moore, Amy Geraldine; Wagner, Paul J. U.S. Pat. Appl. Publ. (2007), 49 pp]

Step 1.
N-(3,5-Dimethoxyphenyl)-2,2,2-trifluoroacetamide

To 3,5-dimethoxyaniline (20 g, 131 mmol) dissolved in anhydrous tetrahydrofuran (90 mL) was added 4-(dimethylamin) pyridine (1.6 g, 13.1 mmol) and ethyl trifluoroacetate (47 mL, 392 mmol). After refluxing 48 hours, the cooled reaction mixture was concentrated and partitioned between ethyl acetate (300 mL) and 2N hydrochloric acid (100 mL). The ethyl acetate layer is washed with water (100 mL), dried using anhydrous sodium sulfate, and concentrated to yield N-(3,5-dimethoxyphenyl)-2,2,2-trifluoroacetamide (31.8 g, 98%) as a pale yellow solid.

Step 2. N-(4-Acetyl-3,5-dimethoxyphenyl)-2,2,2-trifluoroacetamide

To a solution of N-(3,5-dimethoxyphenyl)-2,2,2-trifluoroacetamide (31.8 g, 130 mmol) in anhydrous methylene chloride (450 mL), cooled in an ice bath, is added a solution of tin (IV) chloride (29.9 mL, 260 mmol dissolved in 30 mL anhydrous methylene chloride) dropwise over 10 minutes. Acetyl chloride (9.1 mL, 130 mmol) is added slowly, maintaining the temperature of the reaction below 5° C. After stirring 3 hours at room temperature, the reaction is cooled in an ice bath. Water (300 mL) is added, maintaining the temperature of the reaction below 25° C., and the reaction is stirred at room temperature for 18 hours. The reaction mixture is extracted with methylene chloride, and the organic layer is separated, washed with water, dried, filtered and evaporated under reduced pressure. The residue is purified by silica gel column chromatography eluting with 20% to 30% hexanes/ethyl acetate to yield N-(4-acetyl-3,5-dimethoxyphenyl)-2,2,2-trifluoroacetamide (4.8 g, 13%) as a white solid.

Step 3. 1-(4-Amino-2,6-dimethoxyacetophenone)

To N-(4-Acetyl-3,5-dimethoxyphenyl)-2,2,2-trifluoroacetamide (4.3 g, 14.8 mmol) dissolved in methanol (90 mL) is added anhydrous potassium carbonate (4.67 g, 33.8 mmol). After refluxing for 18 hours, the reaction mixture is cooled and concentrated under reduced pressure. The concentrate is extracted with ethyl acetate and the organic layer was washed with brine, dried, filtered and concentrated under reduced pressure to yield 4-amino-2,6-dimethoxyacetophenone (2.5 g, 87%) as a pale yellow solid.

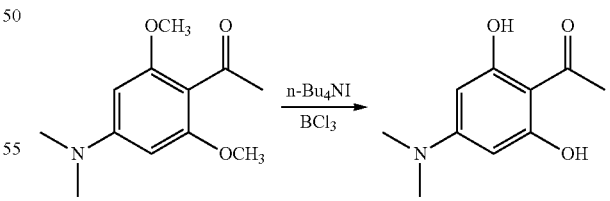

4-Dimethylamino-2,6-hydroxyacetophenone [Brooks P R, Wirtz C, et al. J. Org. Chem. 1999, 64:9719-21]

4-Amino-2,6-dimethoxyacetophenone and n-tetrabutylammonium iodide is stirred in methylene chloride at −78 C. A solution of boron trichloride in methylene chloride is added and the solution is then stirred at 0° C. for 1 hr. The reaction is quenched with ice-water and stirred for 30 min, diluted with saturated sodium bicarbonate, and extracted with methylene chloride. The combined extracts are dried and purified by chromatography on silica gel to provide 4-dimethylamino-2,6-hydroxyacetophenone.

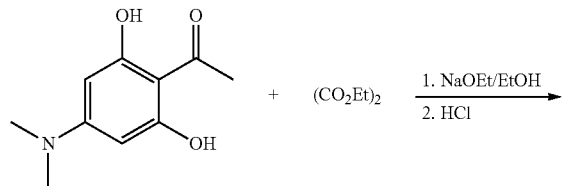

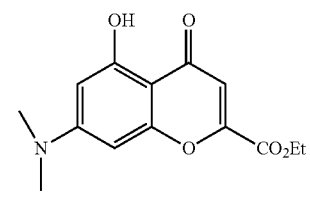

or

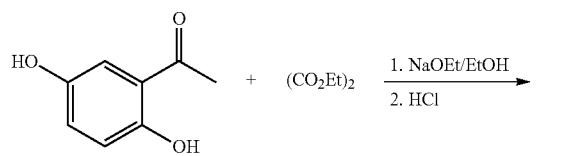

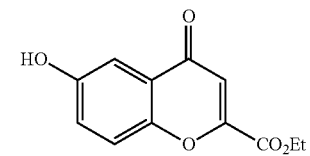

2-Carbethoxy-3-dimethylamino-5-hydroxy-γ-chromone ethyl ester or 2-Carbethoxy-4-hydroxy-γ-chromone ethyl ester A mixture of 4-dimethylamino-2,6-hydroxyacetophenone (or 2,5-dihydroxy-acetophenone) (Sigma-Aldrich) and ethyl oxalate in ether is added to a solution of sodium ethoxide in ethanol. The mixture is stirred at 25° C. for 30 min, heated at reflux for 1.5 hr, cooled and filtered. The precipitated sodium salt is washed with ether and dried. It is then dissolved in water and acidified with 10% HCl to form a sticky solid. The solid is refluxed in ethanol (20 mL) with a catalytic amount of 36% HCL for 1 hr. The mixture is poured into 50 mL of water and extracted twice with methylene chloride (50 mL). The extracts are combined and dried. After solvent removal, the crude material is chromatographed on silica gel (ethyl acetate/hexane 20:80) to yield 2-carbethoxy-3-dimethylamino-5-hydroxy-γ-chromone ethyl ester (or 2-carbethoxy-4-hydroxy-γ-chromone ethyl ester).

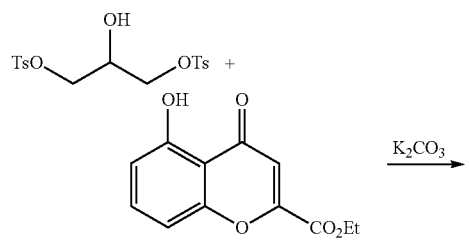

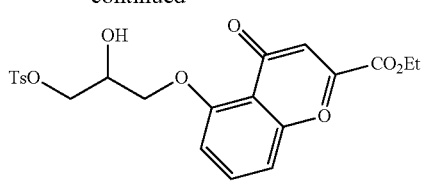

or

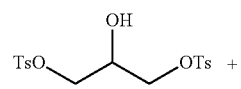

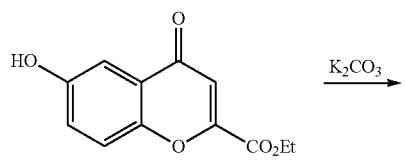

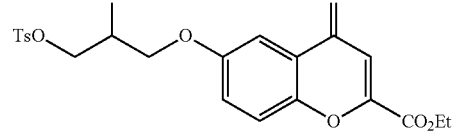

A mixture of 1,3-bis[(tolylsulfonyl)oxy]-2-propanol (1 equivalent), 2-carbethoxy-5-hydroxy-γ-chromone ethyl ester (or 2-carbethoxy-5-hydroxy-γ-chromone ethyl ester) (1 equivalent) and potassium carbonate in N-methyl-2-pyrrolidone (NMP) is heated for 6 hr at 140° C. Once cooled, the mixture is diluted with water and extracted with methylene chloride. Extracts are combined and dried. After solvent removal, the crude material is chromatographed on silica gel to yield product.

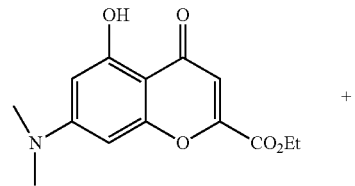

+

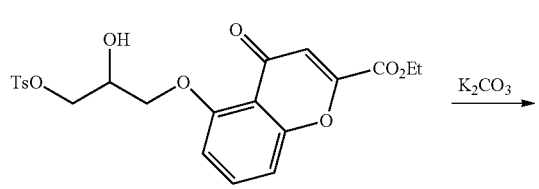

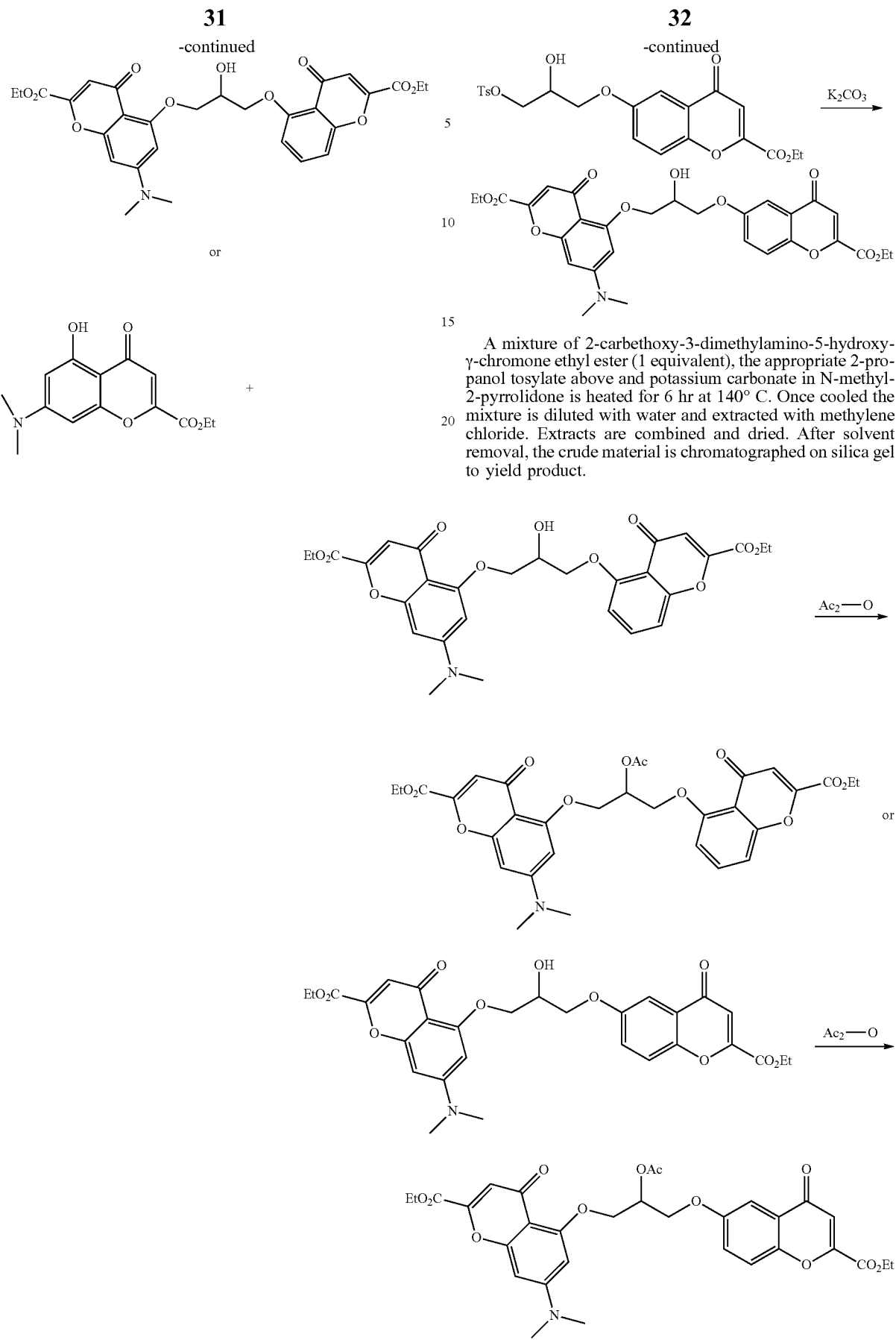

A mixture of 2-carbethoxy-3-dimethylamino-5-hydroxy-γ-chromone ethyl ester (1 equivalent), the appropriate 2-propanol tosylate above and potassium carbonate in N-methyl-2-pyrrolidone is heated for 6 hr at 140° C. Once cooled the mixture is diluted with water and extracted with methylene chloride. Extracts are combined and dried. After solvent removal, the crude material is chromatographed on silica gel to yield product.

Example 7

Acetylation of Cromolyn Derivatives

A solution of the cromolyn derivative in methylene chloride and pyridine is treated with acetic anhydride at 0° C. and then allowed to warm to 25° C. where it is stirred for 4 hr. The mixture is washed with 10% sodium bicarbonate and dried. The solvents are removed by vacuum and the crude solid is purified by chromatography.

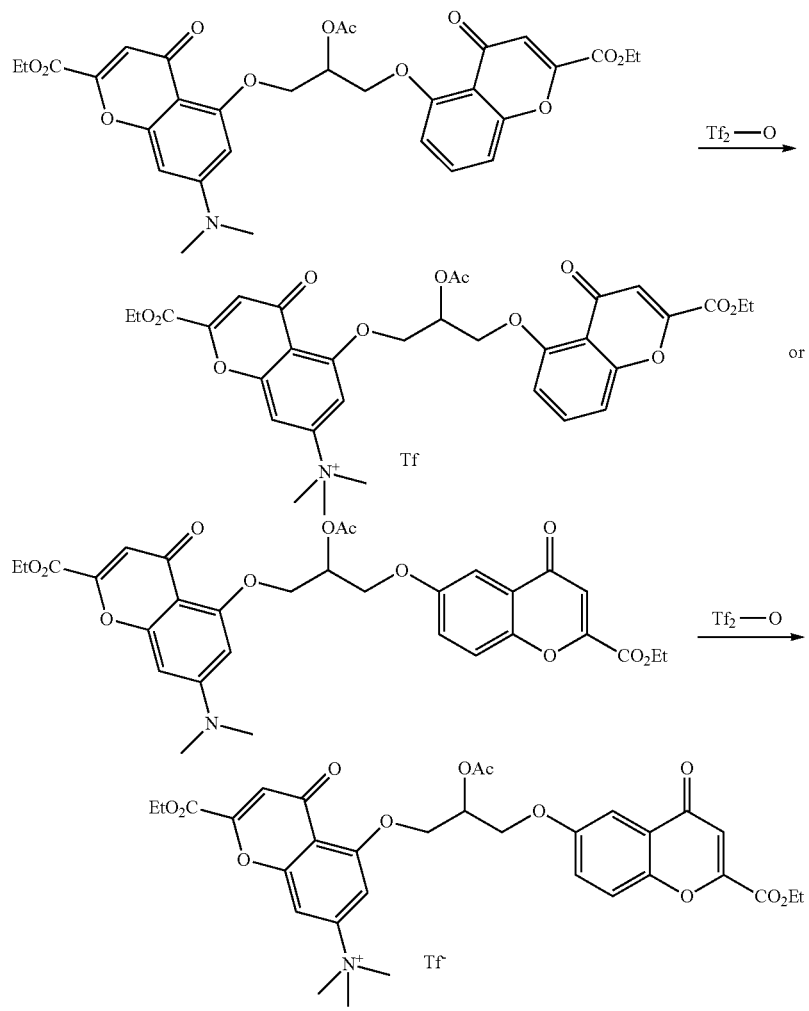

Example 8

Preparation of trimethyl amomonium triflate Salts

A solution of the acetylated cromolyn derivative in methylene chloride is treated with trifluoromethylsulfonic anhydride at 25° C. for 4 hr. The resultant salt is filtered and washed with methylene chloride.

Example 9

Cromolyn derivative (Compound A) inhibits polymerization of Alzheimer's Disease oligomers.

One of the common goals in treating Alzheimer's Disease is to eliminate or reduce the AB oligomers that are the neuron toxins. Achieving this goal slows down Alzheimer's manifestation. One way to demonstrate the efficacy of a drug to treat Alzheimer's is to test for the inhibition of the polymerization of the AB oligomers.

The study described in this example was based on the assay described by Findeis, et al. "Modified-peptide inhibitors of amyloid beta-peptide polymerization." Biochemistry 1999, 38 (21), 6791-800.

AB Peptide: 50 μM of HCl salt or Test compound (Compound A): 50 μM
Buffer: 10 mM sodium phosphate, 100 mM NaCl, pH 7.4
Readout polymerization at: OD 405 nm The results showed that amyloid beta-peptide polymerization in the presence of cromolyn derivative (Compound A) is 2.5 times slower than amyloid beta-peptide polymerization in the presence of a control vehicle.

TABLE 2

| Experimental results | | |
|---|---|---|
| Compound | Time | Relative increase |
| Vehicle (no Add) | 7.97 | (1.0) |
| TS734 (Compound A) | 19.9 | 2.5 |

*Time is elapsed time to 50% of maximum signal
*Relative increase is time(sample)/time(vehicle)

The data above indicate that exemplary Compound A exhibits appreciable brain uptake and clearance and, in terms of efficacy, inhibits AB peptide polymerization. Compound A and related chemical entities are therefore useful for treatment of Alzheimer's Disease in human subjects.

Example 10

Synthesis of 5,5'-(2-[18F]fluorotrimethylenedioxy)bis(4-oxochromene-2-carboxylic acid) sodium salt

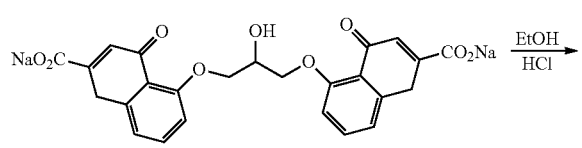

1

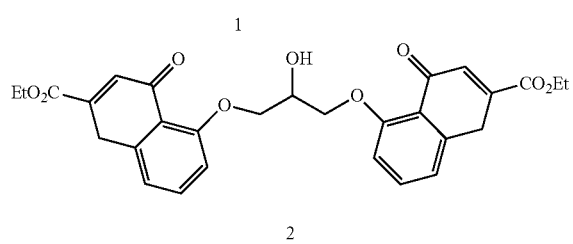

2

5,5'-(2-Hydroxytrimethylenedioxy)bis(4-oxochromene-2-carboxylic acid) diethyl ester A suspension of cromolyn sodium salt 1 (161 mg, 0.31 mmol) in ethanol (25 mL) and conc. HCl (1 mL) was heated in a sealed flask for 28 h at 95-100° C. The suspension dissolved to give a clear colorless solution. Solvent was evaporated and the crude oil was chromatographed on silica gel using 100% ethyl acetate to yield the diethyl ester 2 (132 mg, 80%): TLC Rf=0.44 (100% ethyl acetate); 1HNMR (CDCb, 300 MHz) δ 1.42 (t, 3H, J=7.1 Hz, CH3), 2.73 (br s, 1H, OH), 4.44 (q, 4H, J=7.1 Hz, 2OCH2CH3), 4.324.59 (m, 5H, CHOH, 2OCH2), 6.93-6.99 (rn, 4H, 2 vinyl H, 2 aromatic H), 7.16 (d, 2H, J=8.4 Hz, aromatic H), 7.59 (t, 2H, J=8.2 Hz, aromatic H)

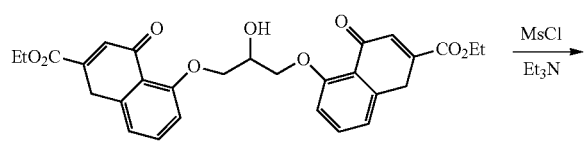

2

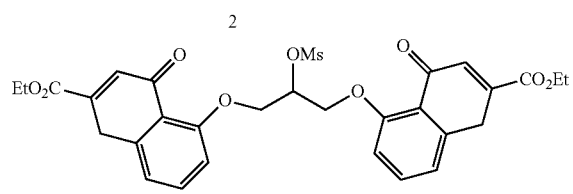

3

1,3-bis(2-(ethoxycarbonyl)-4-oxo-4H-chromen-5-yloxy)propan-2-yl methanesulfonate A solution of the alcohol 2 (107 mg, 0.20 mmol) and triethylamine (41 mg, 0.41 mmol) in dichlormethane (25 mL) cooled to 0° C. was treated with methanesulfonyl chloride (34 mg, 0.30 mmol). After stirring for 2 h at 0° C., methylene chloride (100 mL) was added and the mixture was washed with satd. NaHC03 (2×30 mL) and brine (50 mL), dried over MgS04, and concentrated. The residue was purified by flash column chromatography (80% ethyl acetate in hexane) to give the product 3 (102 mg, 84%): TLC R.=0.54 (ethyl acetate); 1H NMR (CDCI3, 300 MHz δ 1.39 (t, 3H, J=7.1 Hz, CH3), 3.35 (s, 3H, CH3S02), 4.41 (q, 4H, J=7.2 Hz, 2OCH2CH3), 4.55-4.66 (m, 4H, 2OCH2, 5.40 (quintet, 1H, J=5.0, CHOMs), 6.89 (s, 2H, vinyl H), 6.98 (d, 2H, J=8.4 Hz, aromatic H), 7.16 (d, 2H, J=8.8 Hz, aromatic H), 7.61 (t, 2H, J=8.2 Hz, aromatic H); 13C NMR (CDCb, 75 MHz, Ib=1.0 Hz) δ: 14.3, 38.6, 63.1, 68.7, 77.9, 108.7, 111.8, 115.6, 116.4, 135.2, 150.7, 158.0, 160.7, 177.7.

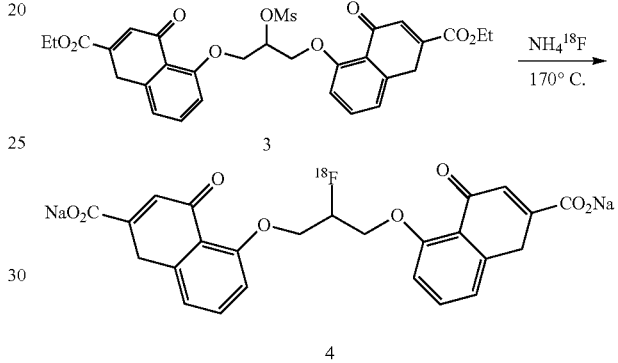

4

5,5'-(2-[18F]Fluorotrimethylenedioxy)bis(4-oxochromene-2-carboxylic acid) sodium salt A Wheaton 5-mL reaction vial containing fluorine-18 (100 mCi) in 1 mL 180-enriched water, and ammonium hydroxide (100 ul) was heated at 120° C. and water was evaporated with the aid of a nitrogen gas flow. The contents were dried by the addition of 1 mL of acetonitrile followed by evaporation of solvent using a nitrogen flow. This process is repeated three times. A solution of 3 mg of mesylate 3 in 0.1 mL of acetonitrile was added to the sealed vial and fluorination was performed at 170° C. for 10 min. Once cooled to room temperature, the reaction mixture was passed through a silica gel Sep-Pak using methylene chloride (3 mL) and the solvent was removed using a nitrogen flow. A mixture of 0.5 mL 1 M lithium hydroxide and 1 mL methanol was added to the reaction vial and the vial heated at 80° C. for 20 min. Solvent was removed and 15,5'-(2-[18F]fluorotrimethylenedioxy)bis(4-oxochromene-2-carboxylic acid) sodium salt was purified on a C18 Sep-Pak using PBS, ph 7, and the solution was filtered (MillexGV 0.22 urn). Radiochemical yield ranged for 5 to 20% EOB.

Example 11

Synthetic Route for Asymmetric Cromolyn

This example illustrates the inventors' general route for synthesis of asymmetric cromolyn derivatives.

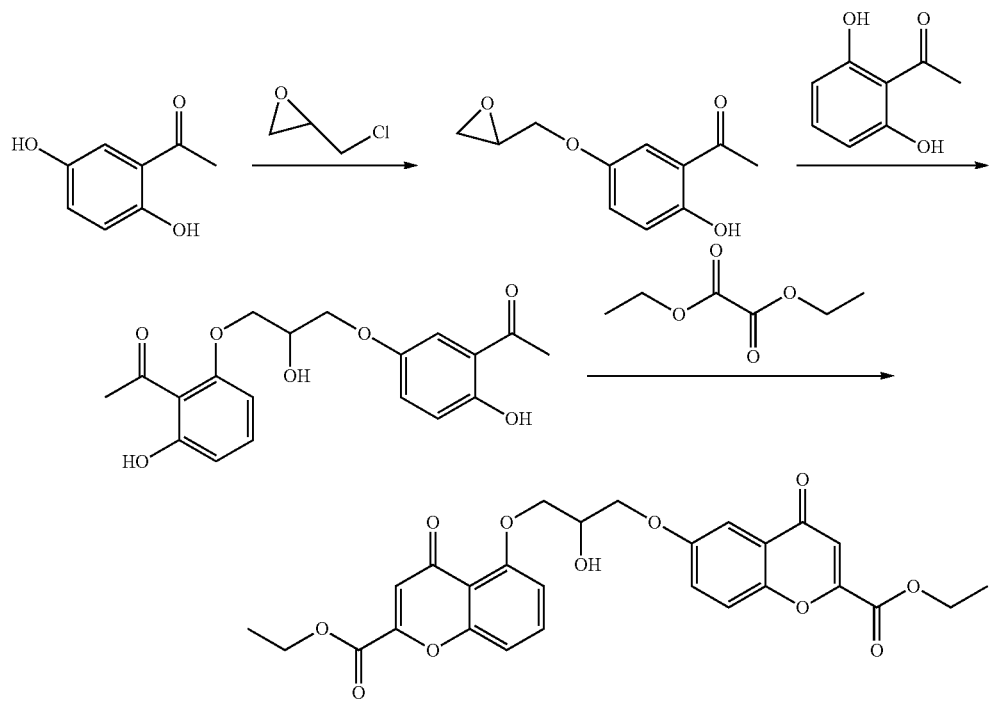

Example 12

In Vivo Experiments of Cromolyn and Ibuprofen Combination Treatment

Three mice groups (five animals in each) were tested in a Morris water navigation test. Two groups were four months young APP/PS1 including a mutant Aβ mouse and a model indicative of Alzheimer's Disease progression. One APP/PS1 group was treated with Cromolyn and ibuprofen combination for six months, and the second was untreated as an control group and a third untreated wild type was used as a normal control. FIG. 1 is a graph showing the in-vivo study summary. WT (wild type, right panel) shows normal untreated mice. The control group (left panel) shows transgenic mice that did not received drug treatment. The treated group (Mid panel) shows transgenic mice that received AZLT-OP1(cromolyn+ibuprofen) for six month by Intraperitoneal (IP) injection twice weekly. Mice were trained for 7 days to remember the location of the platform. At day 8, the platform was removed, and the times of crossing the platform area was recorded.

In another study, 7.5 month old APP/PS1 mice completed treated for a week as an acute treatment using three different doses of Cromolyn Sodium (1.05 mg/kg, 2.1 mg/kg and 3.15 mg/kg). The treatment was given by IP injection everyday for 7 days before sacrificing the mice and harvesting the brain. Brain extracts were quantified for the total amount of Aβ40, Aβ42 and Aβ oligomers.

Here are the main conclusions of this acute study:
1. A dose-dependent decrease in the amount of Aβ40 and Aβ42 associated with the two higher doses (2.1 mg/kg and 3.15 mg/kg), up to 50% was observed.
2 This effect was sustained after treatment of the samples with guanidine-HCl to dissolve any amyloid aggregates.
3 The quantification of oligomeric species using the 82E1/82E1 ELISA kit failed to show any significant difference among the experimental groups.

One explanation to the insignificant change is that acute exposure to Cromolyn Sodium treatment primarily affects monomeric species, impacting oligomers or higher-order aggregates chronic longer treatment term. Acute treatment would not cause a substantial change in the oligomeric quantities.

Example 13

In another experiment, cromolyn derivatives were tested as inhibitors of AP polymerization. Inhibiting Aβ oligomer production will provide of Alzheimer's Disease and treating Alzheimer's Disease.

The investigational product ALZT-OP1a (cromolyn sodium) is a synthetic chromone derivative that has been approved for use by the FDA since the 1970s for the treatment of asthma. For asthma treatment, cromolyn sodium powder was micronized for inhalation to the lungs via dry powder inhaler, i.e. the Spinhaler device. Liquid intranasal and ophthalmic formulations have also been developed for the treatment of rhinitis and conjunctivitis.

The mechanism of action for cromolyn sodium (ALZT-OP1a) is characterized as a mast cell stabilizer, namely to suppress cytokine release from activated lymphocytes together with preventing the release of histamine from mast cells (Netzer, 2012; Keller, 2011). It was administered four times daily as prophylaxis for allergic and exercise-induced asthma, not as a treatment for acute attacks.

Applicants have discovered a new mechanism of action for cromolyn, which, along with its role for suppressing immune responses, enables the re-purposing of this approved drug for use to halt AD progression. The Applicants' studies have shown that cromolyn sodium binds to beta-amyloid peptides and inhibits its polymerization into oligomers and higher order aggregates. The inhibition of beta-amyloid polymerization will arrest amyloid-mediated intoxication of neurons and restore the passage of these aberrant beta-amyloid oligomers out of the brain rather than their accumulation.

Applicants' studies showed that cromolyn or its derivatives penetrates the blood-brain barrier in animal models, so that plasma bioavailability following cromolyn inhalation will translate to concentrations in the brain sufficient to interfere with beta-amyloid oligomerization and accumulation. Inhalation of cromolyn sodium was shown to be the most effective non-injected administration route for systemic bioavailability of cromolyn sodium in animals and humans (Moss, 1970; Neale, 1986; Richards, 1987; Aswania, 1999; Tronde, 2003). An FDA-approved route of administration for cromolyn sodium is oral inhalation using a capsule-based dry powder inhaler, with 20 mg cromolyn sodium loaded per capsule. Studies have shown that with high inspiratory rates, the inhaled cromolyn sodium is delivered efficiently to the human lung, with 10-15% of the inhaled drug-delivered-dose absorbed into the bloodstream (Richards, 1987; Keller, 2011). For these reasons, cromolyn sodium inhalation with a dry powder inhaler device was selected as the route of administration in the present invention. However, plasma levels of cromolyn following inhalation are reported to show high intra- and inter-subject variability, and that cromolyn uptake by asthmatics was lower than in healthy volunteers (Richards, 1987; Keller, 2011).

For planned human studies, each blister will contain the active product ingredient (cromolyn sodium) and inhalation grade lactose monohydrate as an excipient. The once-daily cromolyn dose to be tested in this study is less than 20% the dose from the four-times daily approved dose level (80 mg cromolyn sodium total per day) for the treatment of asthma.

Taken together, the once daily ALZT-OP1a dose in this study should preserve the drug's excellent safety and tolerability profile, yet is predicted to achieve the nanomolar drug concentrations needed to block beta-amyloid oligomerization in the brain to prevent Alzheimer's disease progression.

Example 14

Cromolyn derivatives for inhibiting polymerization of Alzheimer's Disease oligomers.

Figure 2A:
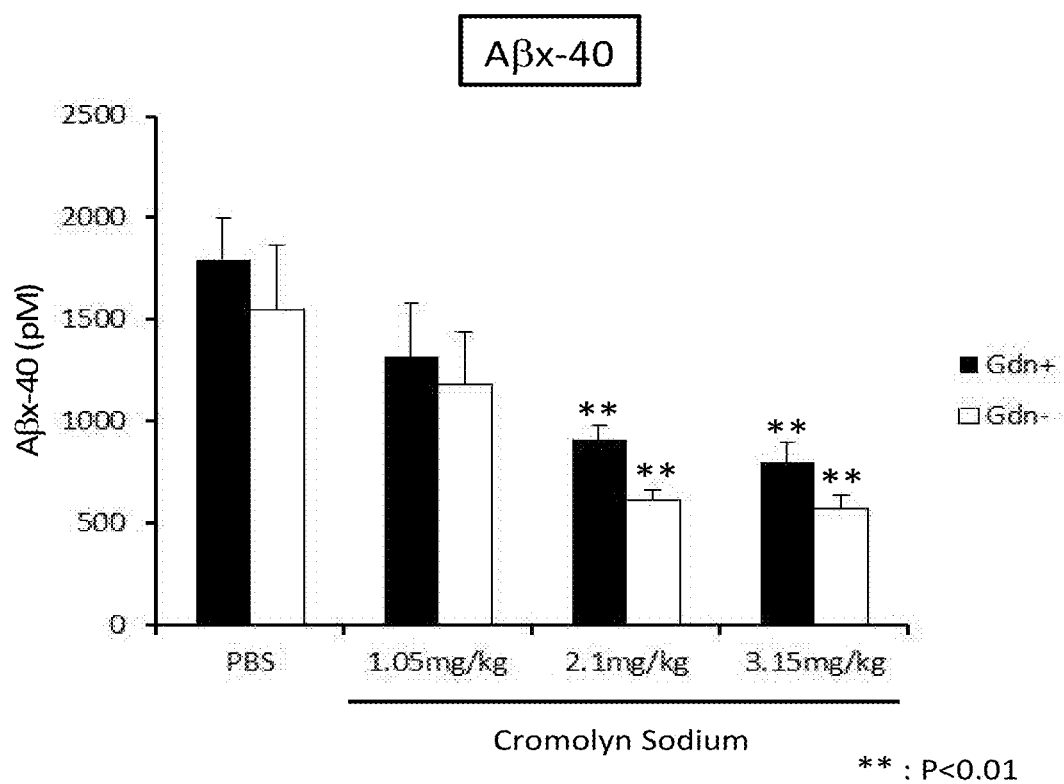
FIG. 2A and FIG. 2B illustrate the measurement of TBS soluble Aβ level by WAKO ELISA. The experiments show that TBS Aβ level decreases following by treatment of cromolyn sodium with dose-dependency.
Figure 2B:
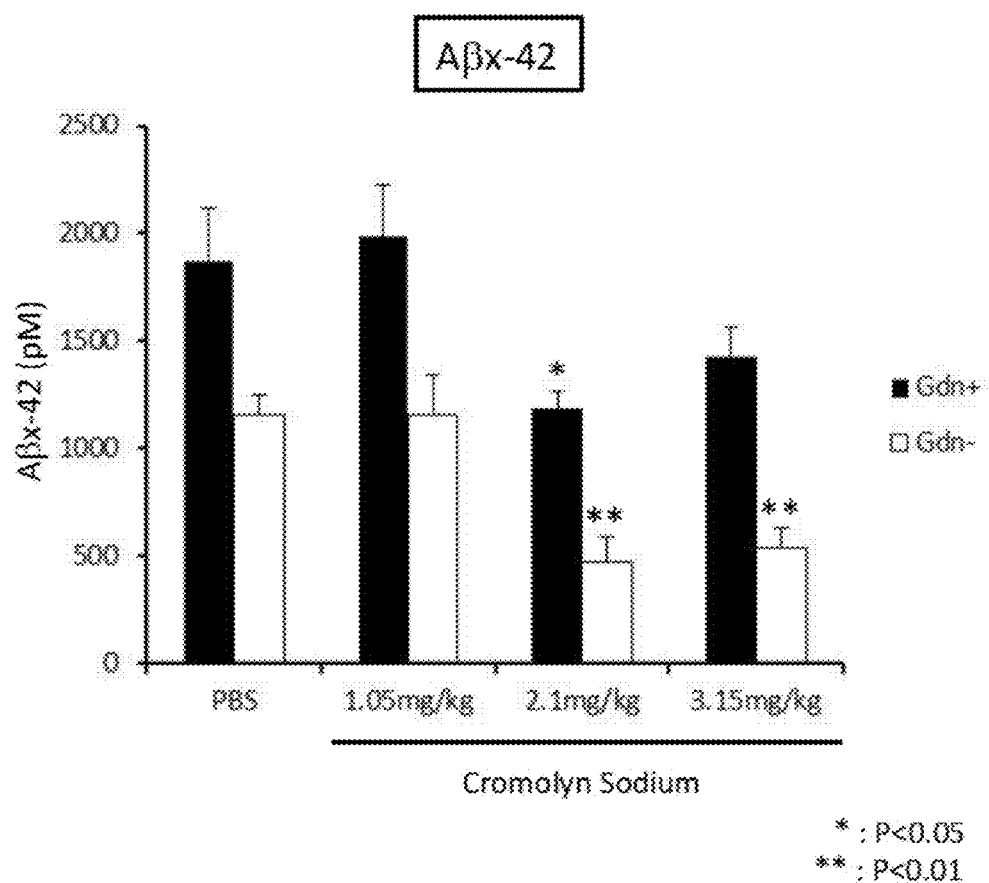

FIG. 2A and FIG. 2B illustrate the measurement of TBS soluble Aβ level by WAKO ELISA. The experiments show that TBS Aβ level decreases following by treatment of cromolyn sodium with dose-dependency. FIG. 2A shows that Aβ40 level decreases following by treatment of cromolyn sodium with dose-dependency. FIG. 2B shows that Aβ42 level decreases following by treatment of cromolyn sodium with dose-dependency. As indicated, the number of animals per group is N=3 or 5, average±SE. The p value is significant using one-way ANOVA test (Bonferroni's test). Both of total soluble Aβ [as shown as Gdn+ (Guanidine-HCl)] and monomeric Aβ [as shown as Gdn− (no guanidine)] decease after the addition of cromolyn sodium. The dose of 2.1 mg/kg of cromolyn sodium was enough to decrease TBS soluble Aβ.

Figure 3A:
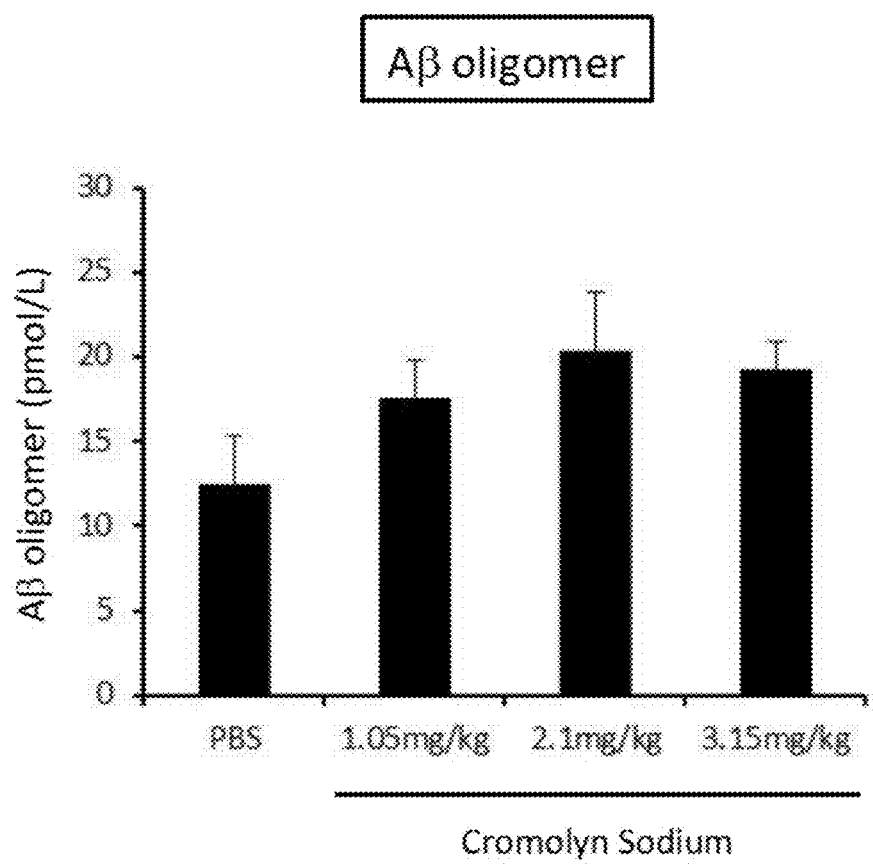
FIG. 3A, FIG. 3B, and FIG. 3C illustrate the measurement of TBS soluble Aβ oligomer level IBL oligomer ELISA. The experiments show that Aβ oligomer level was not changed following the treatment with cromolyn sodium.
Figure 3B:
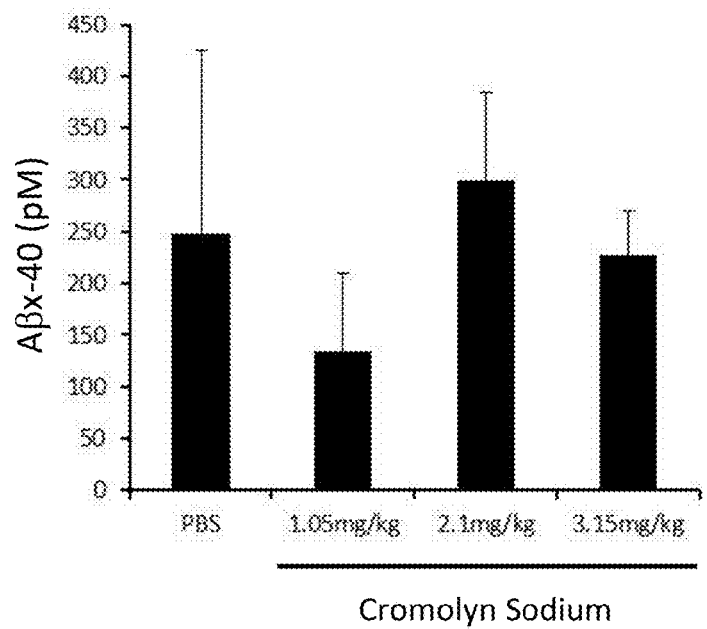
Figure 3C:
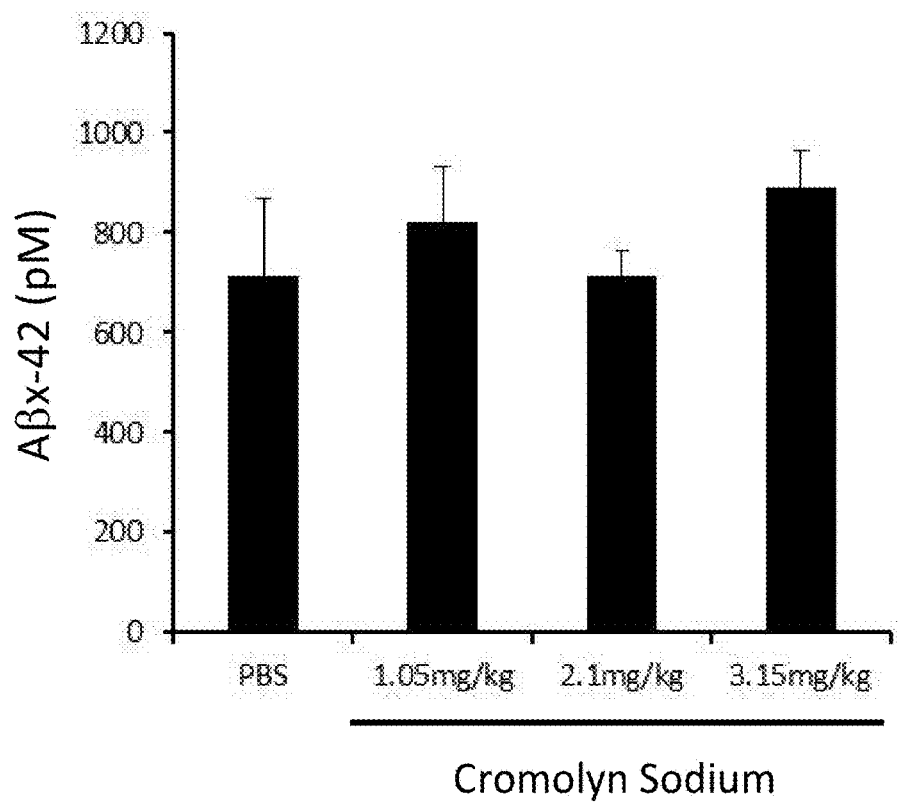

FIG. 3A, FIG. 3B, and FIG. 3C illustrate the measurement of TBS soluble Aβ oligomer level IBL oligomer ELISA (82E1-82E1). The experiments show that AP oligomer level was not changed following the treatment of cromolyn sodium. FIG. 3A shows the experiments of IBL Aβ oligomer ELISA (82E1-82E1). FIGS. 3B and 3C show the difference the experiments with Gdn and those without Gdn using Aβ WAKO ELISA. N=3 or 5 animals per group, average±SE. The p value is not significant using one-way ANOVA test (Bonferroni's test). Both ELISA (IBL oligomer ELISA and the differences between with and without Gdn using WAKO ELISA) showed that oligomer level was not changed following the treatment of cromolyn sodium.

Example 15

Discussion

Applicants summarize the rationale behind the treatment utility of cromolyn as follows:

1. Molecular structure is similar to some that had affinity to plaque (Formula III and table 3). The significant difference is that the drug in the present invention works in nanomolar concentrations as compared to micromolar concentrations of other previous drugs.

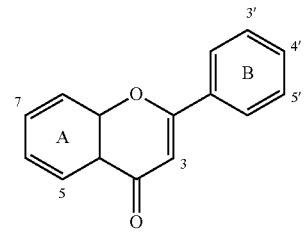

(III)

TABLE 3

The structural similarity of fisetin analogues and their effects on Aβ fibril formation.

| Compound | Substituents | | | | | | Effects on Aβ fibril formation |
|---|---|---|---|---|---|---|---|
| | 3 | 5 | 7 | 3' | 4' | 5' | |
| Fisetin | OH | H | OH | OH | OH | H | Inhibitory |
| 3',4',7-Trihydroxyflavone | H | H | OH | OH | OH | H | Inhibitory |
| 3,3',4'-Trihydroxyflavone | OH | H | H | OH | OH | H | Inhibitory |
| 3,3',7-Trihydroxyflavone | OH | H | OH | OH | H | H | Enhancing |
| 5-Deoxykaempferol | OH | H | OH | H | OH | H | Enhancing |
| Luteolin | H | OH | OH | OH | OH | H | Inhibitory |
| Quercetin | OH | OH | OH | OH | OH | H | Inhibitory |
| Chrysin | H | OH | OH | H | H | H | Enhancing |
| Kaempferol | OH | OH | OH | H | OH | H | Enhancing |
| Myricetin | OH | OH | OH | OH | OH | OH | Inhibitory |

2. The suitable molecular weight of the molecules in the present invention allows the molecules to penetrate brain.

Chemical Structure:

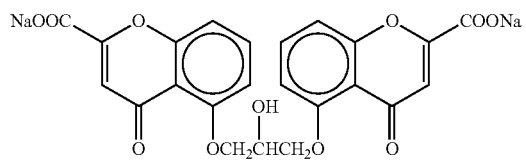

Molecular Formula: $C_{23}H_{14}Na_2O_{11}$
Molecular Weight: 512.34 [g/mol]

3. The molecules in the present invention have desirable lipophilicity (Log P) and pressure surface area (PSA) in the brain penetration range (Table 4). The PIB analog TS3124 has a 4% brain concentration, and a higher Log P value in a range that there is no usal uptake. This is balanced by the much lower PSA. Log P was determined by Chemdraw pro, Version 10. PSA was determined by the previous methods (http://www.daylight.com/meetings/emug00/Ertl/tp-sa.html).

TABLE 4

The molecular structures, molecular weight, lipophilicity (LogP) and pressure surface area (PSA).

| compound | Structure | Mw | logP | PSA | PKa |
|---|---|---|---|---|---|
| TS734 | (structure) | 466.41 | 2.1 | 127.20 | |
| C0399 | (structure) | 508.38 | 1.39 for diacid | 125.43 | |
| TS3124 | (structure) | 302.37 | 3.92 | 45.15 | OH: 9.2 NH: 19.2 |

Figure 4:
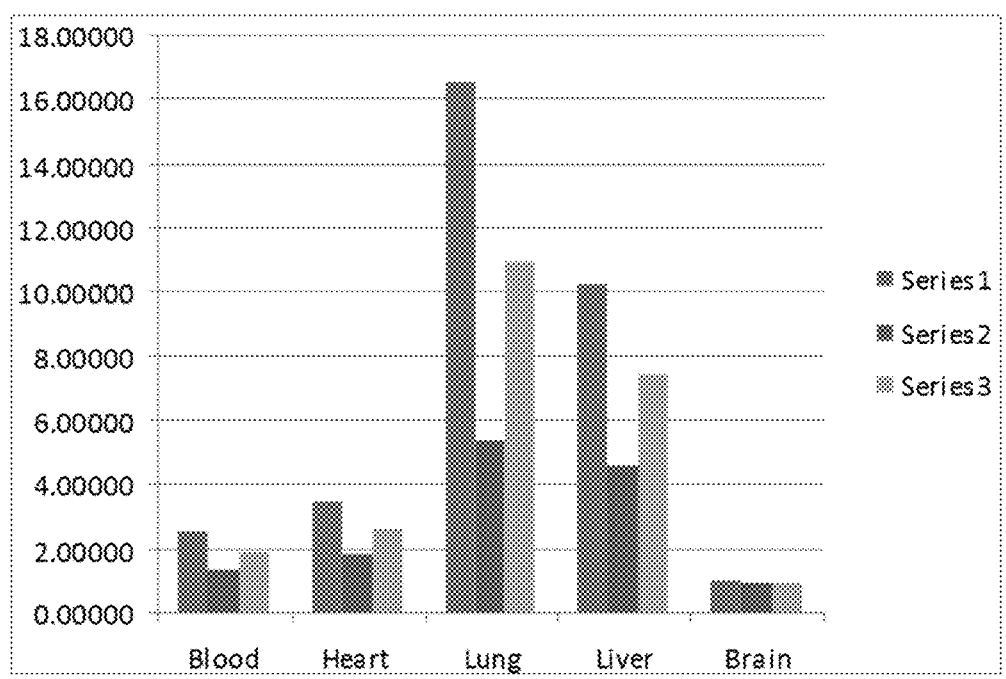
FIG. 4 illustrates the biodistribution of cromolyn Compound A following intravenous injection in mice.

4. Mice biodistribution of radiolabeled cromolyn biodistribution shows 1% dose per gram brain accumulate. FIG. 4 illustrates the biodistribution of radiolabeled cromolyn Compound A following intravenous injection in mice. In FIG. 4, a 5, 30 or 60 minute, corresponding to Series 1, 2 or 3, respectively in the graph, brain uptake shows 1% accumulation with little or no washout for the period measured.

5. The binding of cromolyn to Aβ and its polymerization inhibition was confirmed by four independent methods.

UV Aggregation Assay.

Aβ peptide aggregation and the impact of drugs to slow or prevent AP aggregation was measured by a UV absorbance assay (Findeis, 1999). Aβ (1-40) peptides, at 50 μM, were mixed with 50 μM drug in assay buffer and the plate was incubated at ambient temperature on a plate reader. The UV absorbance was monitored at 540 nm over a 2-3 h period.

Polymerization of Aβ-monomer peptides into clusters of trimers and tetramers initiates the Aβ aggregation process into protofibrils and then into fibrils that form amyloid plaques. The polymerization experiments revealed that Aβ monomer reached 50% polymerization in 14 minutes. At equimolar concentrations with Aβ, the addition of cromolyn inhibited the rate of Aβ polymerization 7-fold, namely 50% polymerization required 75 minutes incubation, compared to 14 minutes in the absence of drug.

TABLE 5

Cromolyn inhibits Aβ polymerization.

| Test Compound | % Thioflavin T Bound | Relative Binding | Relative Increase in Polymerization Time (fold) |
|---|---|---|---|
| Vehicle | 37% | 1 | 1 |
| TS734 (cromolyn) | 30% | 0.82 | 7.8 |

LC/MS/MS Binding Assay.

Binding was measured by equilibrium dialysis. Amyloid fibrils were preformed by incubating the peptide in buffer with shaking for 120 hours at 27° C. The drugs were incubated with fibrils (50 μM peptide) in a RED equilibrium dialysis device (Pierce), and the amount of test agent on each side is determined by LC/MS/MS. Percent bound was calculated as 1−(free conc/total conc) after correcting for background signal. Thioflavin-T was used as a positive control. Binding is displacement of Thioflavin T. Polymerization is ranked for relative Aβ. In general, compounds that rank highly in inhibiting polymerization rank low in binding to aggregates, and vice versa.

Competition Binding Assay.

The competition assay was performed as described previously (Ono and Hayashi, 2009). Amyloid peptide aggregates were preformed by incubating Aβ (1-40) peptide with buffer for 3 days at 37° C. Drugs at 20 μM were mixed with assay solution containing 10 μg/mL amyloid peptide aggregates+3 μM Thioflavin-T on one side of a RED dialysis device with assay buffer added to the other side. After 4 h dialysis, the amount of Thioflavin-T was determined by LC/MS/MS. The relative binding was determined by normalizing the percent binding by the percent binding of the vehicle control.

Aβ Aggregation by Thioflavin T Assay.

One of the most routinely used approaches to monitor Aβ polymerization is the thioflavin T binding assay. When thioflavin T binds to beta-sheet rich structures, such as amyloid aggregates, the dye displays enhanced fluorescence and a characteristic red shift in its emission spectrum. Aβ peptide at 5 μM was mixed with 10 μM thioflavin T with drug at different concentrations. In the absence of drug, Aβ polymerization shows increasing thioflavin T fluorescence over 60-180 min, as shown in FIG. 4.

Figure 5:
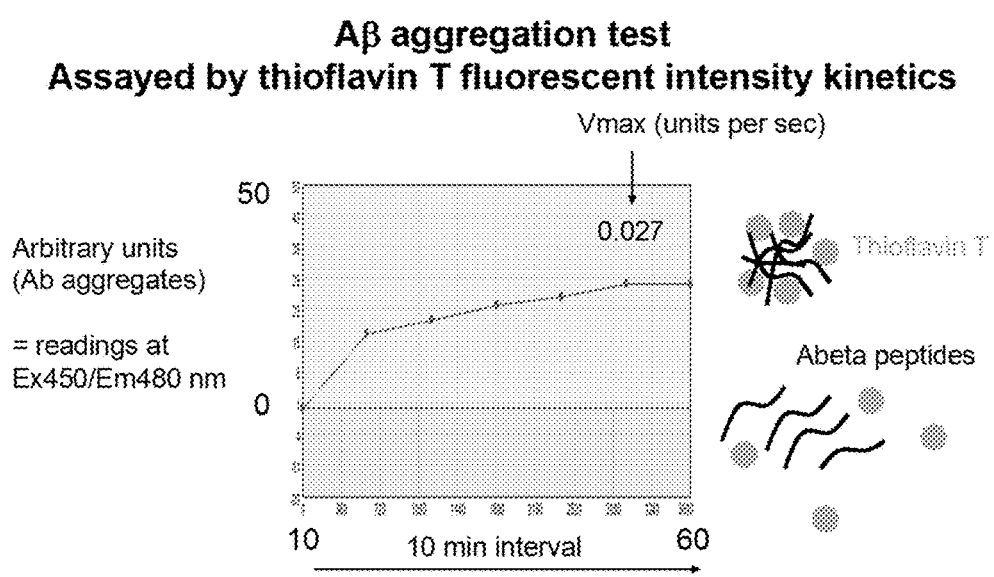
In FIG. 5, a 5, 30 or 60 minute, corresponding to Series 1, 2 or 3, respectively in the graph, brain uptake shows 1% accumulation with little or no washout for the period measured.

The addition of cromolyn (CO399) and its $^{18}$F derivative (TS734) at nanomolar concentration shows inhibition of Aβ aggregation, as shown in FIG. 5.

By four separate in vitro assays, cromolyn sodium, at nanomolar concentrations, effectively inhibits Aβ amyloid peptide polymerization into oligomers and higher order aggregates.

Figure 6:
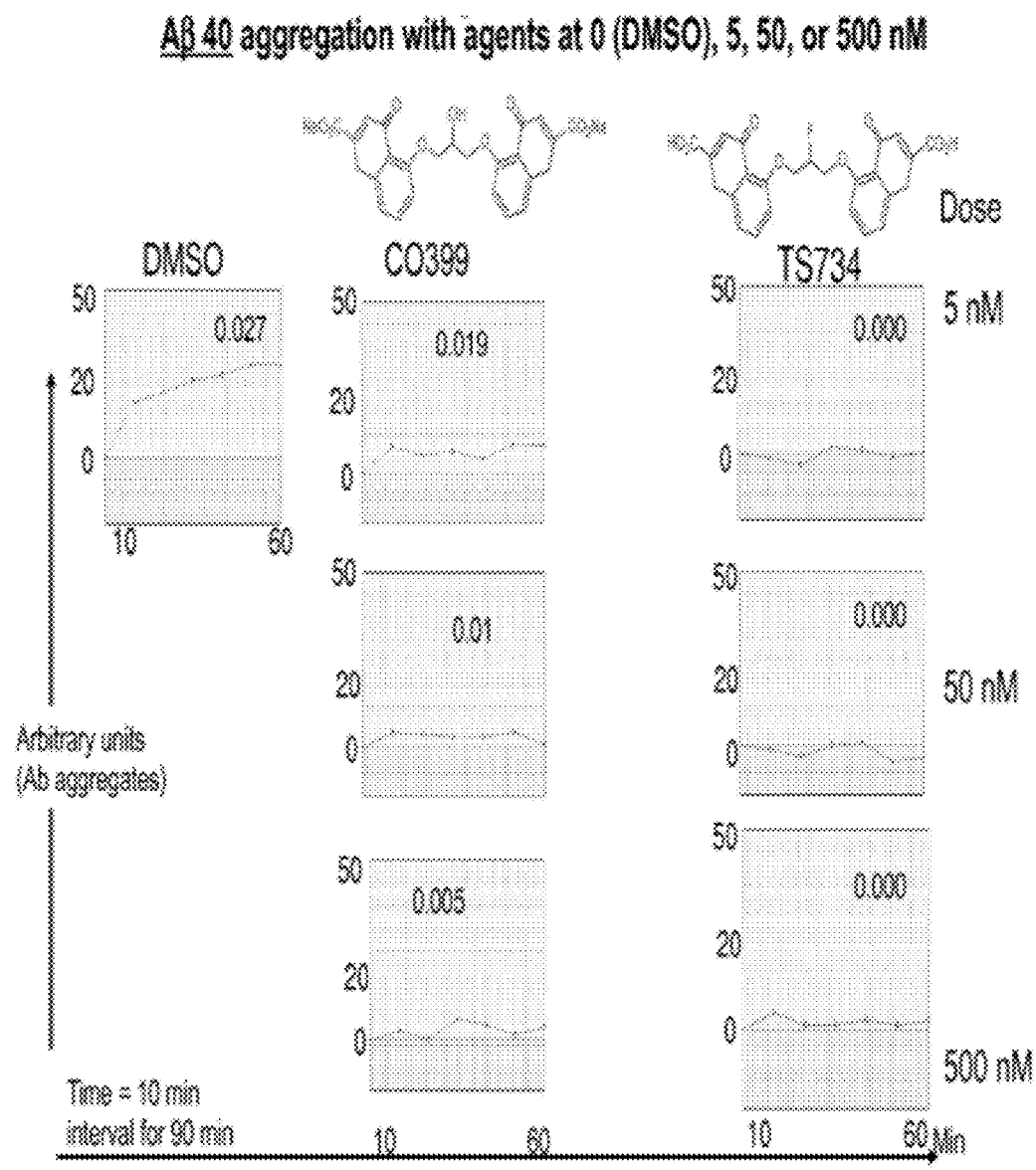
FIG. 6 illustrate Aβ aggregation test after the addition of cromolyn (CO399) or its $^{19}$F derivative (TS734). The addition of cromolyn (CO399) and its $^{19}$F derivative (TS734) at nanomolar concentration shows inhibition of Aβ aggregation.
Figure 7:
FIG. 7 illustrates the side view of the relative structures and locations of cromolyn and Aβ after cromolyn binds Aβ through a binding model simulation.
Figure 8:
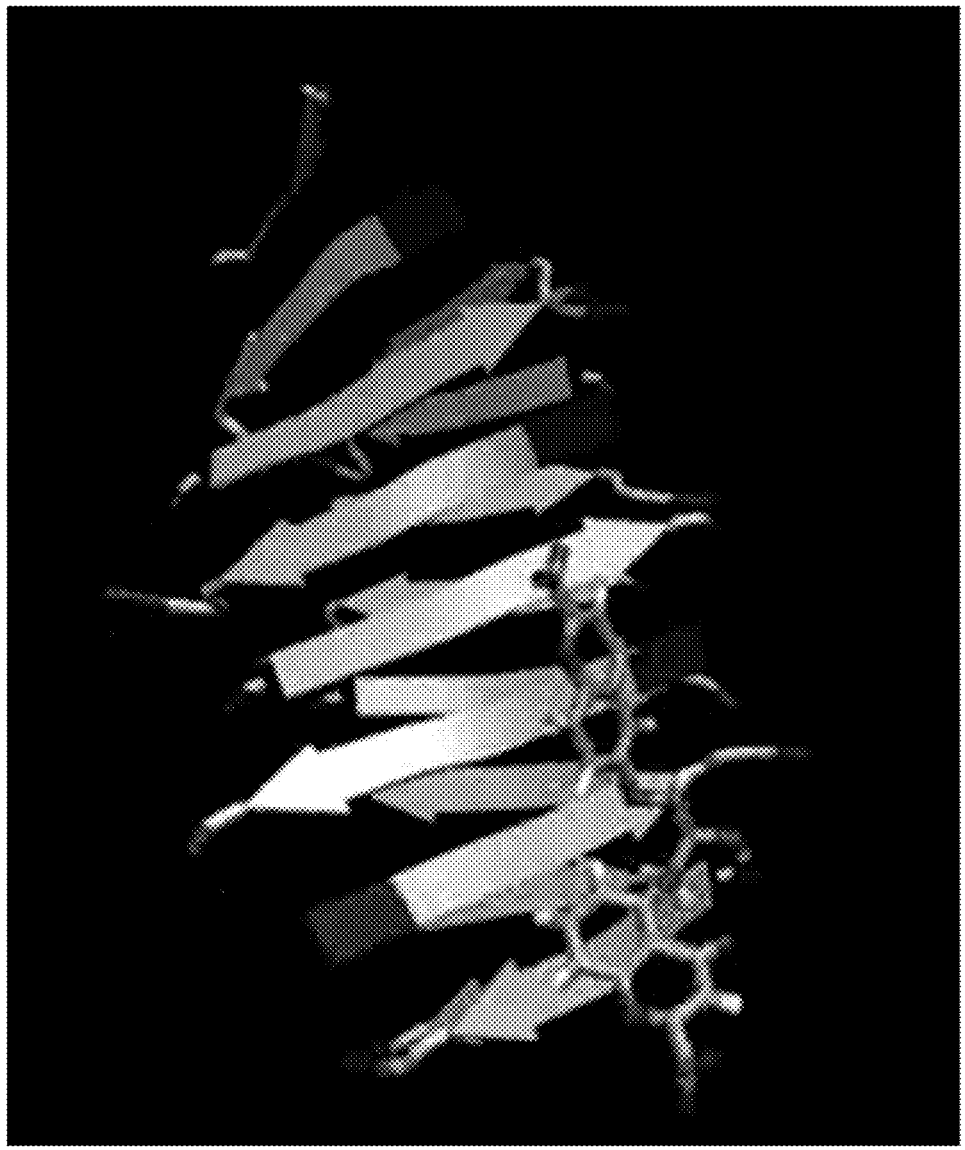
FIG. 8 illustrate the top view of the relative structures and locations of cromolyn and Aβ after cromolyn binds Aβ through a binding model simulation.

6. Preliminary analysis of the binding model indicates that cromolyn binding to the surface of beta sheet across the beta strand in a manner similar to Thioflavin-T. FIGS. 6 and 7 illustrate the side and top view of the relative structures and locations of cromolyn and Aβ after cromolyn binds Aβ through a binding model simulation.

7. Applicants tested several other structures for treating AD in addition to cromolyn. Several types of compounds for both imaging and therapeutic agents have been evaluated for Aβ peptide polymerization inhibition.

In an effort to combine bioavailability and dual function, Applicants have tethered scyllo-inositol, which is transported across the blood-brain barrier and known to bind and neutralize oligomers into soluble complexes (McLaurin, Kierstead, et al., 2006; Sun, Zhang, et al., 2008), to 2-ethyl-8-methyl-2,8-diazospiro-4,5-decan-1,3-dione, a muscarinic M1 receptor agonist (Palacios, Bolliger, et al., 1986). RS-86 was chosen because evidence has shown that it improves cognitive function, mood and social behavior in some AD patients (Wettstein and Spiegel, 1985). M2 receptors function in cholinergic nerve terminals to regulate the release of acetylcholine, whereas M1 receptors are located on post-synaptic cells and facilitate cellular excitation (Mash, Flynn, 1985). Since presynaptic cholinergic neurons degenerate in AD while postsynaptic M1 muscarinic receptors remain intact, the use of long-acting muscarinic agonists like RS-86 has been proposed as a treatment strategy for memory loss. However, RS86 has low brain penetration; combining it with inositol using a linkage which can be metabolized once in the brain may increase bioavailability of the agonist as well as maintaining the beneficial effect of inositol. In the past, both inositol, in the form of 1-fluoro-scyllo-inositol, and RS-86 derivatives have been radiolabeled with F-18 or C-11 as potential PET probes for AD.

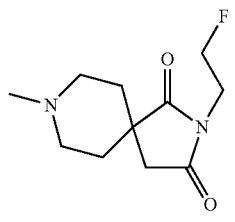
HF203

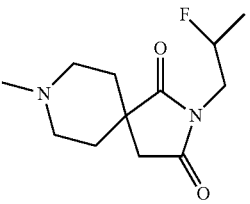
HF83

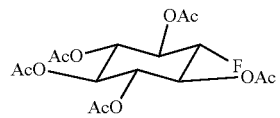
TS6110

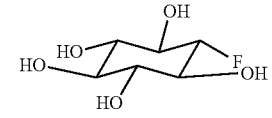
TS6109

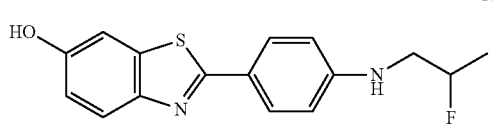 [SMILES: CC(F)CNc1ccc(-c2nc3ccc(O)cc3s2)cc1]
TS3124

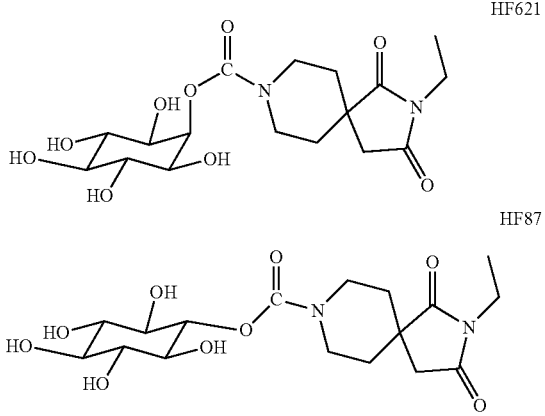

8. It is believed that these suitable compounds target mast cells by inhibiting cytokine production therefore an additional treatment the inflammatory response associated with the AD trigger and process. In their previous publication (Jin, Silverman, et al. 2009), Jin and co-workers indicate that the potential cromolyn compounds can be used as a Mast cell inhibitors.

Example 16

Non-Steroidal Anti-Inflammatory Drugs (NSAIDs).

Compelling evidence from multiple epidemiology studies revealed that long-term dosing with non-steroidal anti-inflammatory drugs (NSAIDs) dramatically reduced AD risk in the elderly, including delayed disease onset, reduced symptomatic severity and slowed cognitive decline (Veld, 2001; Etminan, 2003; Imbimbo, 2010). Three mechanisms have been proposed how NSAIDs inhibit the processes that contribute to AD progression: i) by inhibiting COX activity to reduce or prevent microglial activation and cytokine production in the brain (Mackenzie, 1998; Alafuzoff, 2000; Yan, 2003; Gasparini, 2004; Imbimbo, 2010); ii) by reducing amyloid deposition (Weggen, 2001; Yan, 2003; Imbimbo, 2010); or iii) by blocking COX-mediated prostaglandin E2 responses in synapses (Kotilinek, 2008).

Therefore, NSAIDs are predicted to dampen the neuroinflammatory response and impact AD progression via several mechanisms. When administered together with drugs that inhibit beta-amyloidoligomerization, the combination treatment paradigm is proposed to attenuate the multiple triggers leading to neurodegeneration and neuronal death. The decline in cognitive performance may be reversed, due to neuronal plasticity and neurogenesis in the hippocampus (Kohman, 2013), if AD progression is arrested at a very early stage.

Ibuprofen.

Ibuprofen is a non-selective COX inhibitor for treating inflammation as a non-steroidal anti-inflammatory drug (NSAID). The COX enzymes convert certain fatty acids to prostaglandins. The prostaglandins at the end of the "chain" of reactions that starts with the COX enzyme cause an increased sensitivity to pain, fever, and vasodilation (increased blood flow or inflammation). By inhibiting the start of this chain of reactions, ibuprofen therefore reduces pain, fever, and inflammation. Because ibuprofen blocks the activity of both COX enzymes, it is considered a non-selective COX inhibitor NSAID.

ALZT-OP1 therapy for the treatment of individuals with amnestic mild cognitive impairment. ALZT-OP1 is a multi-functional drug therapy consisting of cromolyn sodium (ALZT-OP1a) administered by inhalation to inhibit beta-amyloid peptide polymerization and to dampen immune responses, plus a concomitant but separately administered low dose oral ibuprofen tablet (ALZT-OP1b) to inhibit the neuro-inflammatory response in persons with confirmed amnestic mild cognitive impairment (aMCI) due to Alzheimer's disease. Both active pharmaceutical ingredient (API) drugs in this ALZT-OP1 formulation are approved, marketed drugs that have been re-purposed for use to prevent the onset of dementia and Alzheimer's disease progression.

ALZT-OP1a

The investigational product ALZT-OP1a (cromolyn sodium) is a synthetic chromone derivative that has been approved for use by the FDA since the 1970s for the treatment of asthma. For asthma treatment, cromolyn sodium powder was micronized for inhalation to the lungs via dry powder inhaler, i.e., the Spinhaler device. Liquid intranasal and ophthalmic formulations have also been developed for the treatment of rhinitis and conjunctivitis.

The mechanism of action for cromolyn sodium (ALZT-OP1a) is characterized as a mast cell stabilizer, namely to suppress cytokine release from activated lymphocytes together with preventing the release of histamine from mast cells (Netzer, 2012; Keller, 2011). It was administered four times daily as prophylaxis for allergic and exercise-induced asthma, not as a treatment for acute attacks.

We have discovered a new mechanism of action for cromolyn, which, along with its role for suppressing immune responses, enables the re-purposing of this approved drug for use to halt AD progression. Our studies have shown that cromolyn sodium binds to beta-amyloid peptides and inhibits its polymerization into oligomers and higher order aggregates. The inhibition of beta-amyloid polymerization will arrest amyloid-mediated intoxication of neurons and restore the passage of these aberrant beta-amyloid oligomers out of the brain rather than their accumulation.

Our studies showed that cromolyn penetrates the blood-brain barrier in animal models, so that plasma bioavailability following cromolyn inhalation will translate to concentrations in the brain sufficient to interfere with beta-amyloid oligomerization and accumulation. Inhalation of cromolyn sodium was shown to be the most effective non-injected administration route for systemic bioavailability of cromolyn sodium in animals and humans (Moss, 1970; Neale, 1986; Richards, 1987; Aswania, 1999; Tronde, 2003). An FDA-approved route of administration for cromolyn sodium is oral inhalation using a capsule-based dry powder inhaler, with 20 mg cromolyn sodium loaded per capsule. Studies have shown that with high inspiratory rates, the inhaled cromolyn sodium is delivered efficiently to the human lung, with 10-15% of the inhaled drug-delivered-dose absorbed into the bloodstream (Richards, 1987; Keller, 2011). For these reasons, cromolyn sodium inhalation with a dry powder inhaler device was selected as the route of administration in this study. However, plasma levels of cromolyn following inhalation are reported to show high intra- and inter-subject variability, and that cromolyn uptake by asthmatics was lower than in healthy volunteers (Richards, 1987; Keller, 2011).

Cromolyn sodium powder blend (ALZT-OP1a) will be loaded into blisters for use with a dry powder inhaler with reproducible aerosol performance at a range of inspiratory rates. Each blister will contain the active product ingredient (cromolyn sodium) and inhalation grade lactose monohydrate as an excipient. The once-daily cromolyn dose to be tested in this study is less than 20% the dose from the four-times daily approved dose level (80 mg cromolyn sodium total per day) for the treatment of asthma. The dose is calculated to titrate the estimated daily 22-27 nanogram of Aβ amyloid plaque produced in the brain.

Taken together, the once daily ALZT-OP1a dose in this study should preserve the drug's excellent safety and tolerability profile, yet is predicted to achieve the nanomolar drug concentrations needed to block beta-amyloid oligomerization in the brain to prevent Alzheimer's disease progression.

ALZT-OP1b (ibuprofen). The generic name is iso-butyl-propanoic-phenolic acid. ALZT-OP1b is an over the counter drug, taken in orally and does not require prescription. Ibuprofen has a long safety history. The drug is used for pain, fever, sports injuries and gastrointestinal problems. The weight dosage independence has been indicated on the drug package.

The investigational product ALZT-OP1b (ibuprofen) is non-selective COX inhibitor for treating inflammation as a non-steroidal anti-inflammatory drug (NSAID). The COX enzymes convert certain fatty acids to prostaglandins. The prostaglandins at the end of the "chain" of reactions that starts with the COX enzyme cause an increased sensitivity to pain, fever, and vasodilation (increased blood flow or inflammation). By inhibiting the start of this chain of reactions, ibuprofen therefore reduces pain, fever, and inflammation. Because ibuprofen blocks the activity of both COX enzymes, it is considered a non-selective COX inhibitor NSAID.

As described above, dampening the neuro-inflammatory response will impact AD progression by several mechanisms. Ibuprofen, which crosses the human blood brain barrier (Bannworth, 1995; Parepally, 2006), dampens the production of pro-inflammatory cytokines (Gasparini, 2004), which should contribute to its utility for preventing AD progression. However, NSAIDs, such as rofecoxib and naproxen, for the treatment of AD has been inconclusive or contributed to higher risk of AD progression when administered as the sole therapy in clinical trials (Thal, 2005; Imbimbo, 2010) despite the multiple epidemiology studies showing reduced AD risk in individuals taking NSAIDs, including ibuprofen (Veld, 2001; Etminan, 2003). Besides the criticism surrounding the choice of rofecoxib and naproxen as the NSAIDs for sole therapy in AD (Gasparini, 2004), the ADAPT rofecoxib/naproxen treatment trial was conducted with subjects exhibiting mild-to-moderate AD (Aisen 2003; Breitner, 2011). Given the epidemiology data, it has been hypothesized that NSAID administration may be beneficial only very early in disease (Imbimbo, 2010; Breitner, 2011). The aMCI patient population is therefore the group that we have selected to be tested in this clinical study.

It is important to note that in the NSAID epidemiology studies, AD risk decrease was restricted to NSAIDs that presumably lower beta-amyloid (42-)peptide levels, such as ibuprofen and indomethacin (Gasparini, 2004; Imbimbo, 2010), and long-term dosing with low NSAID doses were equally effective as higher doses (Broe, 2000; Breitner 2001). Hence, in one cohort in this AZTherapies ALZT-OP1 trial, oral ibuprofen will be administered as tablets (ALZT-OP1b) at a dose lower (less than 5%) of the lowest over-the-counter approved dose. In combination with cromolyn sodium inhalation treatment (ALZT-OP1a), we will test the hypothesis that dampening the low level neuroinflammatory response with ibuprofen will contribute significantly to preventing cognitive decline due to Alzheimer's disease progression. The dose is calculated to titrate the estimated invisible inflammatory response at the early stages of the disease.

Uncontrolled ibuprofen dosage is associated with several side effects such as nausea, headache, ulcers, dizziness, and hypertension. A minor number of cases can cause heart or renal failures. The overdose of ibuprofen can be dangerous. The proposed daily dose for this clinical trial is 20 fold lower than the dose over the counter, and the total yearly dose totaled from the chronic daily dose is less than a total weekly dose over the counter. It is not expected that the yearly toxicity will exceed the weekly over the counter dose.

Risk Benefits of ALZT-OP1 (Cromolyn)

The main goal for using ALZT-OP1 in aMCI subject is its predicted multifunctional treatment of the early appearance signs of cognitive impairment associated with Alzheimer's Disease. Low dose of ALZT-OP1a is expected to control Aβ oligomerization and slow down the extra cellular Aβ fibril brain accumulation. At the same time, low dose of ALZT-OP1a can inhibit cytokine production from the high brain must cell concentration. The low dose ALZT-OP1b (ibuprofen), a known non-specific COX inhibitor, is expected to control the inflammatory response associated with Aβ plaque formation. The main benefits of the low dose chronic daily use are to control and slow down the earlier AD pathophysiology cascade of the main events that trigger intracellular tau tangles and neuron degeneration. ALZT-OP1 treatment will slow down later AD stages manifestation, prolong the patient's life, better control the quality of life and significantly lower the expensive cost of family and nursing treatment and human resources.

Both medications are approved for treatment since the seventies. Both drugs displayed excellent safety profile at much higher dosages. However, each of the drugs have its own short and chronic treatment side effects for the used dosages.

AZLT-OP1a has a long history of safety in adults and children. Cromolyn sodium is available as metered-dose inhalers, and used for long-term asthma prevention ad control by decreasing inflammation and improving lung function. Cromolyn blocks cytokine release of mast cells that cause airways inflammation. The drug is associated with very mild side effects, like coughing, skin rash, and headaches. The treatment doses in this clinical trial are 4-8 folds lower that prescribed and are not expected to cause any significant higher toxicity that the asthma dose.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. American Heart Association: Heart Disease and Stroke Statistics 2004.
2. Libby P. Inflammation in Atherosclerosis. *Nature.* 2002; 420:868-74.
3. Fernex M. The mast-cell system, its relationship to atherosclerosis, fibrosis and eosinophils. Basel, New York, Karger, 1968.
4. Mor A, and Mekori Y A. Mast Cells and Atherosclerosis. *Israel Medical Association Journal;* 2001; 3:216-221.
5. Kelly J L, Chi O S, Abou-Auda W, Smith J K, Krishnaswamy G. The molecular role of mast cells in atherosclerotic cardiovascular disease. *Mol Med Today.* 2000; 6:304-08.
6. Sun J, Sukhova G K, Wolters P J, Yang M, Kitamoto S, Libby P, MacFarlane L A, Mallen-St Clair J, Shi G P. Mast cells promote atherosclerosis by releasing proinflammatory cytokines. *Nature Medicine* 2007; 13, 719-724.
7. Huang M, Pang X, Letourneau R, Boucher W, Theoharides T C. Acute stress induces cardiac mast cell activation and histamine release, effects that are increased in Apolipoprotein E knockout mice. *Cardiovascular Research* 2002 55(1):150-160.
8. Gilman A G, Rail T W, Nies A S, et al., editors. Goodman and Gilman's the pharmacological basis of therapeutics. 8th ed. New York: Pergamon Press; 1990. p. 630-1; Murphy S. Cromolyn sodium: basic mechanisms and clinical usage. *Pediatr Asthma Allergy Immuno/*1988; 2: 237-54.
9. Bot I, de Jager S C, Zernecke A, Lindstedt K A, van Berkel T J, Weber C, Biessen E A. Perivascular mast cells promote atherogenesis and induce plaque destabilization in apolipoprotein E-deficient mice. *Circulation.* 2007; 115: 2516-2525.
10. Huang M, Pang X, Karalis K, Theoharides T C. Stress-induced interleukin-6 release in mice is mast cell-dependent and more pronounced in Apolipoprotein E knockout mice. *Cardiovascular Research* 2003 59(1):241-249.
11. Findeis et al., "Modified-Peptide Inhibitors of Amyloid β-Peptide Polymerization," *Biochemistry* 1999, 38, 6791-6800
12. Findeis and Molineaux, "Design and Testing of Inhibitors of Fibril Formation," Methods in Enzymology, 1999, 309, 476-488
13. Netzer N. C. et al, "The acctual role of sodium cromoglycate in the treatment of asthma—a critical review" *Sleep Breath* (2012) 16, 1027-1032.
14. Keller, M. and Shierholz, J. "Have inadequate delivery systems hampered the clinical success of inhaled disodium cromoglycate? Time for reconsideration" (2011) 8, 1-17.
15. Moss, G. F. and Ritchie, J. T., "The Adsorption and Clearance of Disodium Cromoglycate from the Lung in Rat, Rabbit, and Monkey" *Toxicol. Applied Pharmacol.* (1970) 17, 699-707.
16. Neale, M. G. et al, "The pharmacokinetics of sodium cromoglycate in man after intravenous and inhalation administration". *Br. J. Clin. Pharmacol.* (1986) 22: 373-382.
17. Richards, et. al, "Absorption and Disposition Kinetics of Cromolyn Sodium and the Influence of Inhalation Technique". *J. Pharmacol. Exp. Therapeutics* (1987) 241, 1028-1032.
18. Aswania, O. A. et al, "Relatively bioavailability of sodium cromoglycate to the lung following inhalation, using urinary excretions". *J. Clin. Pharmacol.* (1999) 47, 613-618.
19. Tronde, A. et al, "Pulmonary Absorption Rate and Bioavailability of Drugs In Vivo in Rats: Structure-Absorption Relationships and Physicochemical Profiling of Inhaled Drugs" *J. Pharm. Sci.* (2003) 92, 1216-1233.

20. Jin Y, Silverman A J, Vannucci S J. "Mast cells are early responders after hypoxia-ischemia in immature rat brain." *Stroke*. 2009 September; 40(9):3107-12.
21. Aisen P. S. et al, "Effects of Rofecoxib or Naproxen vs. Placebo on Alzheimer Disease Progression" *JAMA* (2003) 289, 2819-2826.
22. Alafuzoff, I. et al, "Lower counts of Astroglia and Activated Microglia in Patients with Alzheimer's Disease with Regular Use of Non-Steroidal Anti-inflammatory Drugs" *J. Alz. Dis.* (2000) 2, 37-46.
23. Albert K. S. and Gernaat, C. M., "Pharmacokinetics of ibuprofen" *Am. J. Med.* (1984a) 13, 40-46.
24. Albert, K. S. et al, "Effects of age on clinical pharmacokinetics of ibuprofen" *Am. J. Med.* (1984b) 13, 47-50.
25. Aswania, O. A. et al, "Relatively bioavailability of sodium cromoglycate to the lung following inhalation, using urinary excretions". *J. Clin. Pharmacol.* (1999) 47, 613-618.
26. Bannworth, B. "Stereoselective disposition of ibuprofen enantiomers in human cerebrospinal fluid" *Br. J. Clin. Pharmacol.* (1995) 40, 266-269.
27. Beach, J. E. et al, "Cromolyn Sodium Toxicity Studies in Primates" *Toxicol. Appl. Pharmacol.* (1981) 57, 367-400.
28. Breitner, J., "Alzheimer's disease: the changing view" *Annals Neurol.* (2001) 49, 418-419.
29. Breitner, J. C. et al, "Extended results of the Alzheimer's disease anti-inflammatory prevention trial" *Alz. Dementia* (2011) 402-411.
30. Broe, G. A. et al, "Anti-inflammatory drugs protect against Alzheimer's disease at low doses". *Arch Neurol.* (2000) 57, 1586-1591.
31. Cummings, J. L., "Alzheimer's Disease". *N Engl J Med* (2004) 351, 56-67.
32. Doody, R. S. et. al., "Donepezil treatment of patients with MCI". *Neurology* (2009) 72, 1555-1581.
33. Davies, N. M. "Clinical Pharmacokinetics of Ibuprofen: the first 30 years" *Clin Pharmacokinetics* (1998) 34, 101-158.
34. Etminan, M. et. al., "Effect of non-steroidal anti-inflammatory drugs on risk of Alzheimer's disease: systematic review and meta-analysis of observational studies". *Brit. Med. Journal* (2003) 327, 1-5
35. Gasparini, L. et al, "Non-steroidal anti-inflammatory drugs (NSAIDs) in Alzheimer's disease: old and new mechanisms of action". *J. Neurochem* (2004) 91, 521-536.
36. Griffin, T. S., "What causes Alzheimer's?" *The Scientist* (2011) 25, 36-40.
37. Gwin, E. et al, "Cromolyn sodium in the treatment of asthma associated with aspirin hypersensitivity and nasal polyps" *Chest* (1977) 72, 148-153.
38. Haass, C. and Selkoe, D. J., "Soluble protein oligomers in neurodegeneration: lessons from the Alzheimer's amyloid β-peptide". *Nature Reviews Mol. Cell Biol.* (2007) 8, 101-112.
39. Hashimoto, T. et al, "Apolipoprotein E, especially Apolipoprotein E4, Increases the Oligomerization of amyloid beta Peptide", *J. Neurosci.* (2012) 32, 15181-15192.
40. Heneka, M. et al, "Acute treatment with the PPARγ agonist pioglitazone and ibuprofen reduces glial inflammation and Aβ 1-42 levels in APPV717I transgenic mice". *Brain* (2005) 128, 1442-1453.
41. Hoozemans, J. J. M., et al, "Soothing the Inflamed Brain: Effect of Non-Steroidal Anti-Inflammatory Drugs on Alzheimer's Disease Pathology". *CNS & Neurological Disorders—Drug Targets* (2011) 10, 57-67.
42. Imbimbo, B. et al, "Are NSAIDs useful to treat Alzheimer's disease or mild cognitive impairment" *Front. Aging Neurosci* (2010) 2 (article 19), 1-14.
43. Karran, E. et al, "The amyloid cascade hypothesis for Alzheimer's disease: an appraisal for the development of therapeutics" *Nature Reviews* (2011) 10, 698-712.
44. Keller, M. and Shierholz, J. "Have inadequate delivery systems hampered the clinical success of inhaled disodium cromoglycate? Time for reconsideration" (2011) 8, 1-17.
45. Knowles, J., "Donepezil in Alzheimer's disease:  an evidence-based review of its impact on clinical and economic outcomes". *Core Evidence* (2006) 1, 195-219.
46. Kohman, R. A. and Rhodes, J. S., "Neurogenesis, inflammation and behavior". *Brain, Behavior, and Immunity* (2013) 27: 22-32.
47. Kotilinek, L. et al, "Cyclooxygenase-2 inhibition improves amyloid-β-mediated suppression of memory and synaptic plasticity". *Brain* (2008) 131: 651-664.
48. Krstic, D. and Knuesel, I., "Deciphering the mechanism underlying late-onset Alzheimer disease", *Nature Reviews Neurology*, (2012): 1-10.
49. Mackenzie, I. R. and Munoz, D. G., "Nonsteroidal anti-inflammatory drug use and Alzheimer-type pathology in aging". *Neurology* (1998) 50, 986-990.
50. Neale, M. G. et al, "The pharmacokinetics of sodium cromoglycate in man after intravenous and inhalation administration". *Br. J. Clin. Pharmacol.* (1986) 22: 373-382.
51. Parepally, J. M. R. et al, "Brain Uptake of Nonsteroidal Anti-Inflammatory Drugs: Ibuprofen, Flurbiprofen, and Indomethacin" *Pharm. Research* (2006) 23, 873-881.
52. Pehourcq, F. et al, "Diffusion of arylpropionate nonsteroidal anti-inflammatory drugs into the cerebrospinal-fluid: a quantitative structure-activity relationship approach" *Fundamental Clin. Pharmacol.* (2004) 18, 65-70.
53. Petersen, R. C. et al, "Vitamin E and Donepezil for the Treatment of Mild Cognitive Impairment" *N. Engl. J. Med.* (2005) 352, 1-10.
54. Schneider, L. S. and Sano, M., "Current Alzheimer's disease clinical trials: Methods and placebo outcomes" *Alz & Dementia* (2009) 5, 388-397.
55. Thal, L. J. et al, "A Randomized, Double-Blind, Study of Rofecoxib in Patients with Mild Cognitive Impairment" *Neuropsychopharmacology* (2005) 30, 1204-1215.
56. Tronde, A. et al, "Pulmonary Absorption Rate and Bioavailability of Drugs In Vivo in Rats: Structure-Absorption Relationships and Physicochemical Profiling of Inhaled Drugs" *J. Pharm. Sci.* (2003) 92, 1216-1233.
57. Veld, B. et al, "Nonsteroidal Antiinflammatory Drugs and the Risk of Alzheimer's Disease". *N. Engl. J. Med* (2001) 345, 1515-1521.
58. Weggen, S. et al, "A subset of NSAIDs lower amyloidogenic Abeta42 independently of cyclooxygenase activity". *Nature* (2001) 414, 212-216.
59. Yan, Q., et al, "Anti-Inflammatory Drug Therapy Alters β-Amyloid Processing and Deposition in an Animal Model of Alzheimer's Disease" *J. Neurosci.* (2003) 23, 7504-7509.
60. Zlokovic, B, "Neurovascular pathways to neurodegeneration in Alzheimer's disease and other disorders". *Nature Reviews Neurosci.* (2011) 12, 723-738.
61. Ono M, Hayashi S, Kimura H, Kawashima H, Nakayama M, Saji H., "Push-pull benzothiazole derivatives as probes for detecting beta-amyloid plaques in Alzheimer's brains". *Bioorg Med Chem.* 2009 Oct. 1; 17(19):7002-7. doi: 10.1016/j.bmc.2009.08.032. Epub 2009 August 20.
62. McLaurin J, Kierstead M E, Brown M E, Hawkes C A, Lambermon M H, et al. *Nat Med.* 2006 July; 12(7):801-8.
63. Sun Y, Zhang G, Hawkes C A, Shaw J E, McLaurin J, Nitz M. *Bioorg Med Chem.* 2008; 16(15):7177-7184.
64. Wettstein A, Spiegel R. *Psychopharmacology* 1985, 84:572-3.
65. Mash D C, Flynn D D, Potter L T. *Science,* 1985, 228(4703): 1115-7.
66. Palacios, J. M., Bolliger, G., Closse, A., Enz, A., Gmelin, G. & Molanowski, J. (1986). "The pharmacological assessment of RS-86 (2-ethyl 8-methyl-2, 8-diazaspiro[4, 5]-decan-1, 3-dion hydrobromide). Apotent, specific muscarinic acetylcholine receptor agonist". Eur. J. Pharmacol., 125, 45-62.

The invention claimed is:

1. A method for treating neuroinflammation in a subject in need thereof comprising administering by subcutaneous injection a therapeutically effective amount of cromolyn sodium, wherein the subject had Alzheimer's disease.

2. The method of claim 1, further comprising co-administering:

by mouth ibuprofen,
wherein, taken together, the cromolyn sodium and the ibuprofen are therapeutically effective.

3. The method of claim 2, wherein a dose of 1 to 100 mg of ibuprofen is co-administered.

4. The method of claim 2, wherein a dose of 1, 2, 5, 10, or 25 mg of ibuprofen is co-administered.

5. The method of claim 2, wherein a dose of 10 mg of ibuprofen is co-administered.

6. The method of claim 2, wherein a dose of 10 mg of ibuprofen is co-administered once daily.

7. The method of claim 2, wherein a dose of 10 mg of ibuprofen is co-administered twice daily.

8. The method of claim 1, wherein the therapeutically effective amount of cromolyn sodium administered is from about 0.001 to about 500 mg/kg subject body weight per day.

9. The method of claim 1, wherein the therapeutically effective amount of cromolyn sodium administered is from about 0.1 to about 50 mg/kg subject body weight per day.

10. The method of claim 1, wherein the therapeutically effective amount of cromolyn sodium administered is from about 0.5 to about 5 mg/kg subject body weight per day.

* * * * *